United States Patent
Merlet et al.

(10) Patent No.: US 10,872,449 B2
(45) Date of Patent: Dec. 22, 2020

(54) SYSTEM AND METHOD FOR CONSTRUCTING VIRTUAL RADIAL ULTRASOUND IMAGES FROM CT DATA AND PERFORMING A SURGICAL NAVIGATION PROCEDURE USING VIRTUAL ULTRASOUND IMAGES

(71) Applicant: COVIDIEN LP, Mansfield, MA (US)

(72) Inventors: Nicolas J. Merlet, Jerusalem (IL); Oren P. Weingarten, Herzliya (IL)

(73) Assignee: Covidien LP, Mansfield, MA (US)

( * ) Notice: Subject to any disclaimer, the term of this patent is extended or adjusted under 35 U.S.C. 154(b) by 72 days.

(21) Appl. No.: 16/383,888

(22) Filed: Apr. 15, 2019

(65) Prior Publication Data
US 2019/0340800 A1  Nov. 7, 2019

Related U.S. Application Data

(60) Provisional application No. 62/665,667, filed on May 2, 2018.

(51) Int. Cl.
*G06T 11/60* (2006.01)
*G06T 3/00* (2006.01)
(Continued)

(52) U.S. Cl.
CPC ............ *G06T 11/60* (2013.01); *G06T 3/0031* (2013.01); *G06T 5/002* (2013.01); *G06T 15/06* (2013.01);
(Continued)

(58) Field of Classification Search
CPC ......... G06T 7/0012; G06T 2207/30096; G06T 2207/20081; G06T 2207/20084;
(Continued)

(56) References Cited

U.S. PATENT DOCUMENTS

2004/0228529 A1*  11/2004  Jerebko ............... G06T 7/62
                                                    382/173
2007/0165916 A1*  7/2007  Cloutier ............ G06K 9/6278
                                                    382/128

(Continued)

OTHER PUBLICATIONS

Dillenseger, J-L. et al. "Fast simulation of ultrasound images from a CT volume," Computers in Biology and Medicine, 2009, vol. 39 (2), pp. 180-186.

(Continued)

*Primary Examiner* — Ajibola A Akinyemi

(57) ABSTRACT

A system and method for constructing virtual radial ultrasound images from CT data includes receiving CT data, calculating a gradient of the CT data, and obtaining 2D slices by interpolation in 3D. The method further includes calculating transmission and reflection values on each radial line away from a center of each 2D slice to create a lesion image, converting the lesion image to polar, generating random noise in the polar image, and adding random comet tails to the polar image. A background image is created by computing the mean profile along the radius from a series of polar lesion images. The background image is merged with the polar lesion image and random noise is generated in the background of the merged image. Density variations are simulated in the merged image and coordinates of the merged image are transformed to Cartesian to construct a virtual radial ultrasound image.

20 Claims, 16 Drawing Sheets

(51) Int. Cl.
*G06T 5/00* (2006.01)
*G06T 15/06* (2011.01)
(52) U.S. Cl.
CPC ............... *G06T 2207/10081* (2013.01); *G06T 2207/20221* (2013.01); *G06T 2207/30096* (2013.01)
(58) Field of Classification Search
CPC . G06T 2207/10081; G06T 2207/10088; G06T 2207/10116; G06T 2207/30016; G06T 2200/24; G06T 2207/30061; G06T 7/0014; G06T 7/11; G06T 2207/10132; G06T 7/0016; G06T 7/70; G06T 11/006; G06T 5/50; G06T 11/001; G06T 2207/20076; G06T 5/002
USPC .......................................................... 382/128
See application file for complete search history.

(56) References Cited

U.S. PATENT DOCUMENTS

2014/0100440 A1\* 4/2014 Cheline ................ A61B 5/0066
 600/407
2016/0284240 A1 9/2016 Liang

OTHER PUBLICATIONS

Examination Report No. 1 issued in corresponding Australian Patent Application No. 2019202779 dated Jun. 25, 2019, 8 pages.
Feldman, M. et al. "US Artifacts," RadioGraphics, 2009, vol. 29, No. 4, pp. 1179-1189.
Ziskin, M. et al. "The Comet Tail Artifact," Journal of Ultrasound in Medicine, 1982, vol. 1(1), pp. 1-7.
Ciamak Abkai et al: "Real-time simulator for intravascular ultrasound (IVUS)", Proceedings of the SPIE—The International Society for Optical Engineering SPIE—Vertical-Cavity Surface-Emitting Lasers XIII, vol. 6513, Mar. 6, 2007 (Mar. 6, 2007), p. 65131E, XP055626051.
Extended European search report issued in EP Application No. 19172131.5 dated Oct. 10, 2019, 6 pages.
Pio, Rkowski A. et al., "The Transesophageal Echocardiography Simulator Based on Computed Tomography Images", IEEE Transactions on Biomedical Engineering, IEEE Service Center, Piscataway, NJ, USA, vol. 60, No. 2, Feb. 1, 2013 (Feb. 1, 2013), pp. 292-299, XP011514869.
Wein W et al: "Automatic CT-ultrasound registration for diagnostic imaging and image-guided intervention", Medical Image Analysis, Oxford University Press, Oxofrd, GB, vol. 12, No. 5, Oct. 1, 2008 (Oct. 1, 2008), pp. 577-585, XP023783020.

\* cited by examiner

US 10,872,449 B2

SYSTEM AND METHOD FOR CONSTRUCTING VIRTUAL RADIAL ULTRASOUND IMAGES FROM CT DATA AND PERFORMING A SURGICAL NAVIGATION PROCEDURE USING VIRTUAL ULTRASOUND IMAGES

CROSS REFERENCE TO RELATED APPLICATION

The present application claims the benefit of and priority to U.S. Provisional Application Ser. No. 62/665,667, filed on May 2, 2018 the entire contents of which are incorporated herein by reference.

BACKGROUND

Technical Field

The present disclosure relates to a system, apparatus, and method for constructing virtual radial probe endobronchial ultrasound ("radial EBUS") images from CT data, registering the virtual radial EBUS images with CT data, and performing a surgical navigation procedure using the virtual radial EBUS ultrasound images and CT data.

Description of Related Art

There are several commonly applied methods for treating various maladies affecting organs including the liver, brain, heart, lung and kidney. Often, one or more imaging modalities, such as magnetic resonance imaging, ultrasound imaging, computed tomography (CT), as well as others are employed by clinicians to identify areas of interest within a patient and ultimately targets for treatment.

An endoscopic approach has proven useful in navigating to areas of interest within a patient, and particularly so for areas within luminal networks of the body such as the lungs. To enable the endoscopic, and more particularly the bronchoscopic, approach in the lungs, endobronchial navigation systems have been developed that use previously acquired MRI data or CT image data to generate a three dimensional rendering or volume of the particular body part such as the lungs. In particular, previously acquired images, acquired from an MRI scan or CT scan of the patient, are utilized to generate a three dimensional or volumetric rendering of the patient.

The resulting volume generated from the MRI scan or CT scan is then utilized to create a navigation plan to facilitate the advancement of a navigation catheter (or other suitable device) through a bronchoscope and a branch of the bronchus of a patient to an area of interest. Electromagnetic tracking may be utilized in conjunction with the CT data to facilitate guidance of the navigation catheter through the branch of the bronchus to the area of interest. In certain instances, the navigation catheter may be positioned within one of the airways of the branched luminal networks adjacent to, or within, the area of interest to provide access for one or more medical instruments.

In some procedures, after a catheter is navigated to a region of interest or target, a radial ultrasonic probe is positioned through the catheter to obtain radial EBUS images of the region of interest or target. Such radial EBUS images are useful for a clinician to visualize the area of interest and target in real time and confirm that the catheter is properly positioned relative to the target.

Currently, there exist methods for generating simulated ultrasound images from CT data. However, the known methods for generating simulated ultrasound images from CT data do not mimic real device noise and artifacts. Typically, the known methods for generating simulated ultrasound images from CT data attempt to simulate or create noise, using waves and several echoes, some even utilizing copy and paste of ultrasound textures. In particular, the known methods for generating simulated ultrasound images from CT data apply a Perlin noise as an arbitrary noise without considering if it correctly models the observed noise in real images. Because the known methods apply noise in a standard 2D image, with the same characteristics close, or far, from the center of the radial image, the resulting simulated ultrasound images have very thin noise and very few artifacts, creating a much cleaner and less useful image than a real radial EBUS image.

Accordingly, there is a need for a system that can achieve the benefits of simulating radial EBUS images from CT data, while providing greater detail to the simulated radial EBUS images. Additionally, a need exists for a system that incorporates the simulated radial EBUS images in a surgical navigation system to assist clinicians in performing a surgical navigation procedure.

SUMMARY

The present disclosure is directed to a system and method for constructing virtual radial probe endobronchial ultrasound ("radial EBUS") images from CT data, registering the virtual radial EBUS images with CT data or real time ultrasound images (radial or linear), and performing a surgical navigation procedure using the virtual radial EBUS images and CT data. The constructed virtual radial EBUS images may be formed as a composite image with elements extracted from the CT data combined therewith. The constructed virtual radial EBUS images may be used for guidance, training, navigation planning, improved navigation accuracy, navigation confirmation, and treatment confirmation.

As described in greater detail below, the disclosed system and methods model background noise and various types of artifacts in order to be as realistic as possible, finding an underlying probabilistic model to real ultrasound films, reverse engineering from true data. In the methods disclosed herein, as with real images, the noise gets rougher as the distance from the center increases. In order to get a realistic simulation using this approach, most computations are performed in polar coordinates and the final product is converted to Cartesian.

Aspects of the present disclosure are described in detail with reference to the figures wherein like reference numerals identify similar or identical elements. As used herein, the term "distal" refers to the portion that is being described which is further from a user, while the term "proximal" refers to the portion that is being described which is closer to a user.

According to one aspect of the present disclosure, a method for constructing virtual radial ultrasonic images from CT data is provided. The method includes receiving preoperative CT data of a branched luminal network, calculating a gradient of the CT data (for example, calculating a 3D Sobel gradient), obtaining 2D slices of the CT data by interpolation in 3D, calculating transmission and reflection values on each radial line away from a center of each 2D slice to create a lesion image, converting the lesion image to a polar lesion image, generating random noise in the polar lesion image, adding random comet tails to the polar lesion image based on the random noise, creating a background image by computing the mean profile along the radius from a series of polar lesion images, merging the background image with the polar lesion image to create a merged image, generating random noise in the background of the merged image, simulating density variations in the merged image, and transforming the coordinates of the merged image to Cartesian to construct a virtual radial ultrasound image.

The method may further include copying a kernel in the polar lesion image using a model kernel representing what is seen in an isolated reflection. Copying a kernel in the polar lesion image using a model kernel representing what is seen in an isolated reflection may include applying the formula:

$$imLesion(neiY,neiX)=max(imLesion(neiY,neiX), kernel*imReflection(peakY,peakX)),$$

where neiY and neiX are lists of coordinates in a neighborhood of peakY and peakX.

Additionally, the method may further include simulating apparent blurring of real ultrasound images around high density points in the polar lesion image. Simulating apparent blurring of real ultrasound images around high density points in the polar lesion image may include performing a plurality, for example twenty, grey linear closings for a plurality, for example twenty, directions between 0 and 180 degrees.

Calculating transmission and reflection values on each radial line away from a center of each 2D slice to create a lesion image may include applying the formulas:

$$imVirt(ptCur)=|Rad \cdot Grad|\cdot|Grad|/(2 \cdot Vol)^{\wedge}2 \cdot valTransmit,$$

and $$imTransmit(ptCur)=(1-(|Grad|/(2 \cdot Vol))^{\wedge}2.$$

Adding random comet tails to the polar lesion image based on the random noise may include adding a comet to a peak by considering each of the peak's neighbors (neiPeak), above and below, in a kernel mask.

The method may further include copying to the right of the peak's neighbors along a horizontal line a decreasing profile defined for each pixel as:

$$val(neiPeak)*ratioX(radiusDif)*ratioY(angleDif),$$

where radiusDif is the radius difference to the peak and angleDif is the angle difference to the peak for each pixel along the profile.

Merging the background image with the polar lesion image to create a merged image may include applying a heuristic formula, for example, $$imBackground(y,x)=imBackground(y,x)+log(imBackground(y,x))*imLesion(y,x)*K.$$

In yet another aspect of the present disclosure, a system for constructing virtual radial ultrasound images from CT data is provided. The system includes a computing device configured to receive preoperative CT data of a branched luminal network, calculate a gradient of the CT data (for example, calculate a 3D Sobel gradient), obtain 2D slices of the CT data by interpolation in 3D, calculate transmission and reflection values on each radial line away from a center of each 2D slice to create a lesion image, convert the lesion image to a polar lesion image, generate random noise in the polar lesion image, add random comet tails to the polar lesion image based on the random noise, create a background image by computing the mean profile along the radius from a series of polar lesion images, merge the background image with the polar lesion image to create a merged image, generate random noise in the background of the merged image, simulate density variations in the merged image, and transform the coordinates of the merged image to Cartesian to construct a virtual radial ultrasound image.

The computing device may be configured to calculate transmission and reflection values on each radial line away from a center of each 2D slice to create a lesion image by applying the formulas:

$$imVirt(ptCur)=|Rad \cdot Grad|\cdot|Grad|/(2 \cdot Vol)^{\wedge}2 \cdot valTransmit,$$

and $$imTransmit(ptCur)=(1-(|Grad|/(2 \cdot Vol))^{\wedge}2.$$

The computing device may be further configured to copy a kernel in the polar lesion image using a model kernel representing what is seen in an isolated reflection. The computing device may be configured to copy a kernel in the polar lesion image using a model kernel representing what is seen in an isolated reflection by applying the formula:

$$imLesion(neiY,neiX)=max(imLesion(neiY,neiX), kernel*imReflection(peakY,peakX)),$$

where neiY and neiX are lists of coordinates in a neighborhood of peakY and peakX. Additionally, the computing device may be further configured to simulate apparent blurring of real ultrasound images around high density points in the polar lesion image. For example, the computing device is configured to simulate apparent blurring of real ultrasound images around high density points in the polar lesion image by performing a plurality, for example twenty, grey linear closings for a plurality, for example twenty, directions between 0 and 180 degrees.

The computing device may be configured to add random comet tails to the polar lesion image based on the random noise by adding a comet to a peak by considering each of the peak's neighbors (neiPeak), above and below, in a kernel mask.

The computing device may be further configured to copy to the right of the peak's neighbors along a horizontal line a decreasing profile defined for each pixel as:

$$val(neiPeak)*ratioX(radiusDif)*ratioY(angleDif),$$

where radiusDif is the radius difference to the peak and angleDif is the angle difference to the peak for each pixel along the profile. Additionally, the computing device may be configured to merge the background image with the polar lesion image to create a merged image by applying a heuristic formula, for example, $$imBackground(y,x)=imBackground(y,x)+log(imBackground(y,x))*imLesion(y,x)*K.$$

BRIEF DESCRIPTION OF THE DRAWINGS

Various aspects and embodiments of the present disclosure are described hereinbelow with references to the drawings, wherein.

DETAILED DESCRIPTION

The present disclosure is directed to a system and method for constructing virtual radial probe endobronchial ultrasound ("radial EBUS") images from CT data, registering the virtual radial EBUS images with CT data or real time ultrasound images (radial or linear), and performing a surgical navigation procedure using the virtual radial EBUS images and CT data. The constructed virtual radial EBUS images utilize the creation of noise similar to real noise to create a more accurate and more realistic simulation of the images. The constructed virtual radial EBUS images may be formed as a composite image with elements extracted from the CT data combined therewith. The constructed virtual radial EBUS images may be used for guidance, training, navigation planning, improved navigation accuracy, navigation confirmation, and treatment confirmation.

As described in greater detail below, the disclosed system and methods model background noise and various types of artifacts in order to be as realistic as possible, finding an underlying probabilistic model to real ultrasound films, reverse engineering from true data. In the methods disclosed herein, as with real images, the noise gets rougher as the distance from the center increases. In order to get a realistic simulation using this approach, most computations are performed in polar coordinates and the result is converted to Cartesian.

Figure 1:
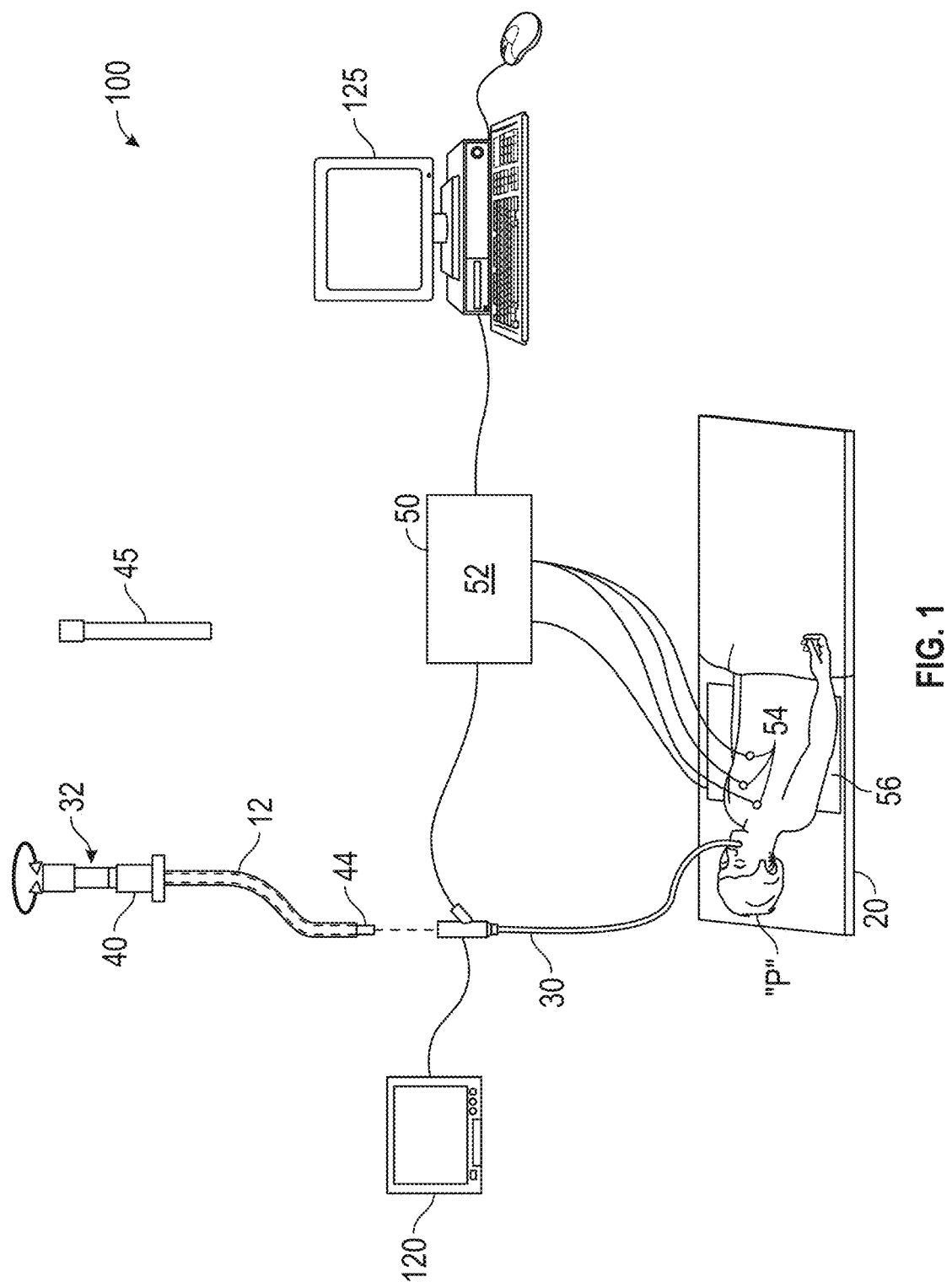
FIG. 1 is a perspective view of one illustrative embodiment of an electromagnetic navigation (EMN) system in accordance with the present disclosure.
Figure 2:
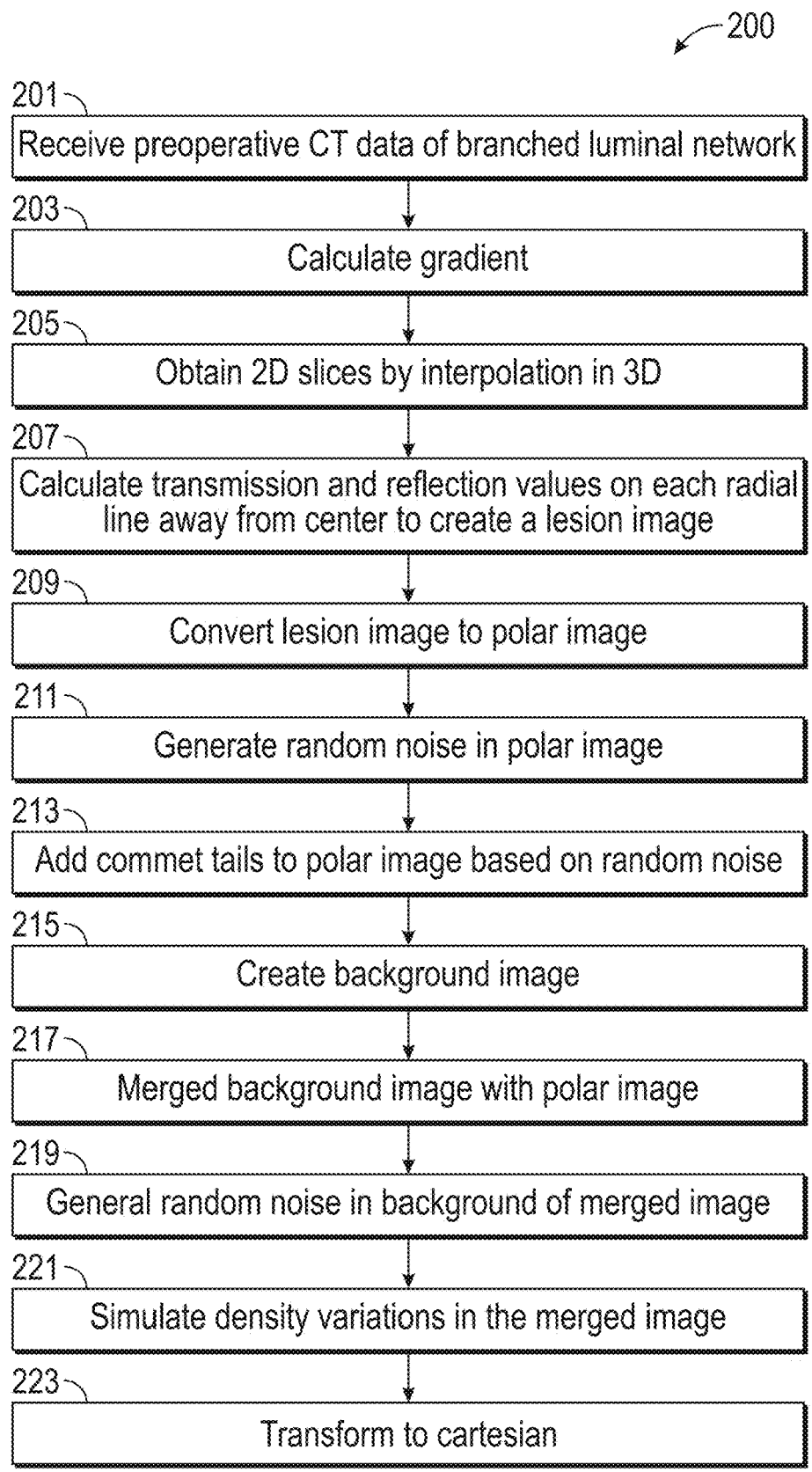
FIG. 2 is a flow chart of a method of constructing virtual radial EBUS images from CT data.

FIG. 1 depicts an Electromagnetic Navigation (EMN) system 100 configured for reviewing CT image data to identify one or more targets, planning a pathway to an identified target (planning phase), navigating an extended working channel (EWC) 12 of a catheter assembly to a target (navigation phase) via a user interface, and confirming placement of the EWC 12 relative to the target. One such EMN system is the ELECTROMAGNETIC NAVIGATION BRONCHOSCOPY® system currently sold by Medtronic PLC. The target may be tissue of interest, or correlate to a position of interest, identified by review of the CT image data during the planning phase. Following navigation, a medical instrument, such as a biopsy tool or other tool, may be inserted into the EWC 12 to obtain a tissue sample from the tissue located at, or proximate to, the target or to treat tissue at, or proximate to, the target.

EMN system 100 generally includes an operating table 20 configured to support a patient "P," a bronchoscope 30 configured for insertion through the patient's "P's" mouth into the patient's "P's" airways; monitoring equipment 120 coupled to bronchoscope 30 (e.g., a video display, for displaying the video images received from the video imaging system of bronchoscope 30); a tracking system 50 including a tracking module 52, a plurality of reference sensors 54 and a transmitter mat 56; and a computing device 125 including software and/or hardware used to facilitate identification of a target, pathway planning to the target, navigation of a medical instrument to the target, and confirmation of placement of an EWC 12, or a suitable device therethrough, relative to the target.

Computing device 125 may be any suitable computing device including a processor and storage medium, wherein the processor is capable of executing instructions stored on the storage medium. The computing device 125 may further include a database configured to store patient data, CT data sets including CT images, fluoroscopic data sets including fluoroscopic images and video, ultrasonic images or data sets, navigation plans, and any other such data. Although not explicitly illustrated, the computing device 125 may include inputs, or may otherwise be configured to receive, CT data sets, fluoroscopic images/video, ultrasonic images/video and other data described herein. Additionally, computing device 125 includes a display configured to display graphical user interfaces. Computing device 125 may be connected to one or more networks through which one or more databases may be accessed and may be configured to perform any of the methods described herein.

As described in further detail below, computing device 125 is configured to create virtual radial EBUS images CT data. The virtual radial EBUS images may be displayed by computing device 125 for enhanced navigation to a target. Further, computing device 125 may also be configured to register the virtual radial EBUS images with real time radial EBUS images acquired by ultrasonic imaging device 45. The registration between the two data sets may be accomplished via image analysis and comparison between the two data sets. Additionally, components of the CT data set may be extracted therefrom and integrated into either or both of the real time ultrasound images received from the radial EBUS probe or the virtual radial EBUS images constructed from the CT data set.

Having briefly described the components of system 100 depicted in FIG. 1, the following description of FIGS. 2-23 provides an exemplary workflow of creating a virtual ultrasonic image, in particular, virtual radial EBUS images, using the components of system 100, and will be described generally as method 200. Any of the methods described herein may be carried out by any component of system 100 and may include all or some of the steps described. Additionally, any of the methods may be carried out in any order, specifically, in a different order of the steps described and illustrated in the figures.

Figure 3:
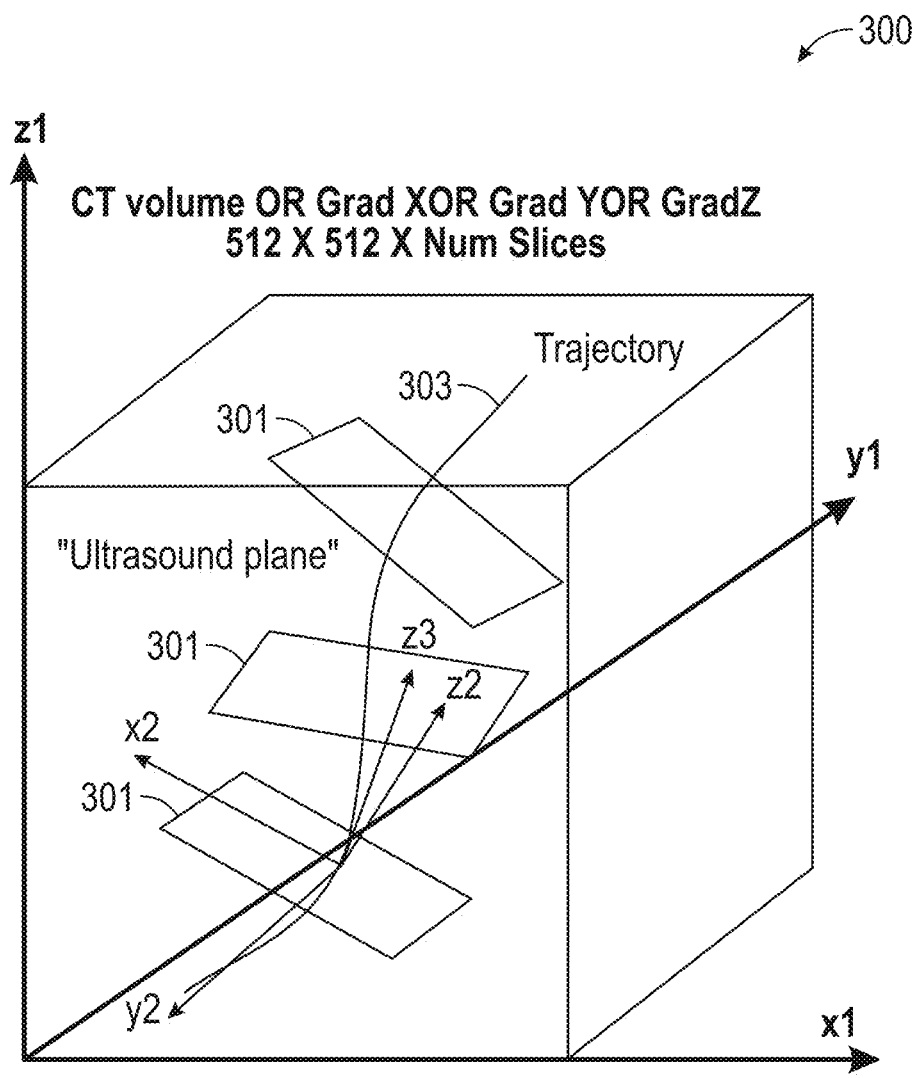
FIG. 3 is an illustration of 2D slices in a 3D gradient/volume.
Figure 5:
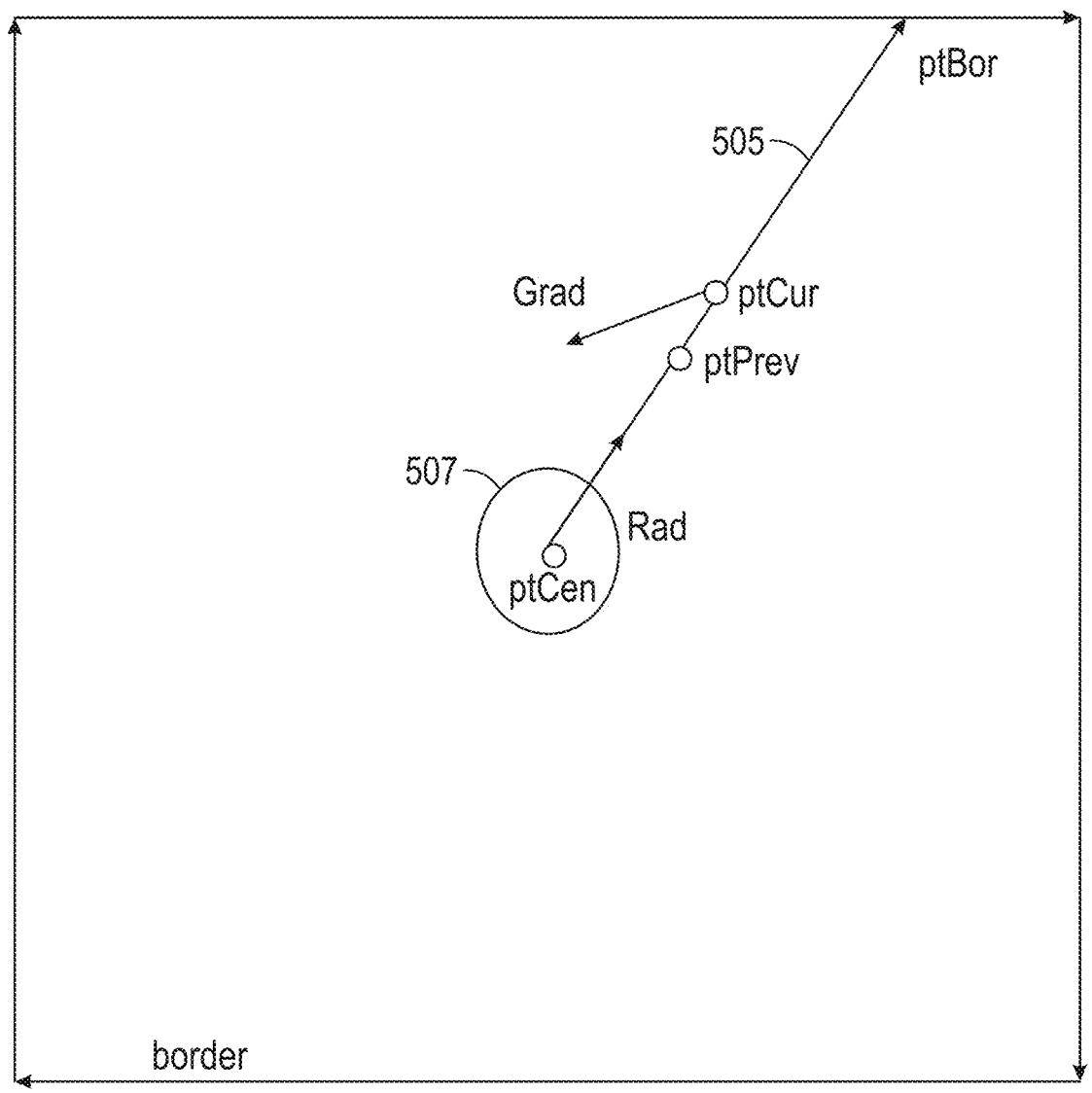
FIG. 5 is an illustration of loops performed from a center point to the border using the formulas described herein to solve for the resulting image ("imVirt")
Figure 7:
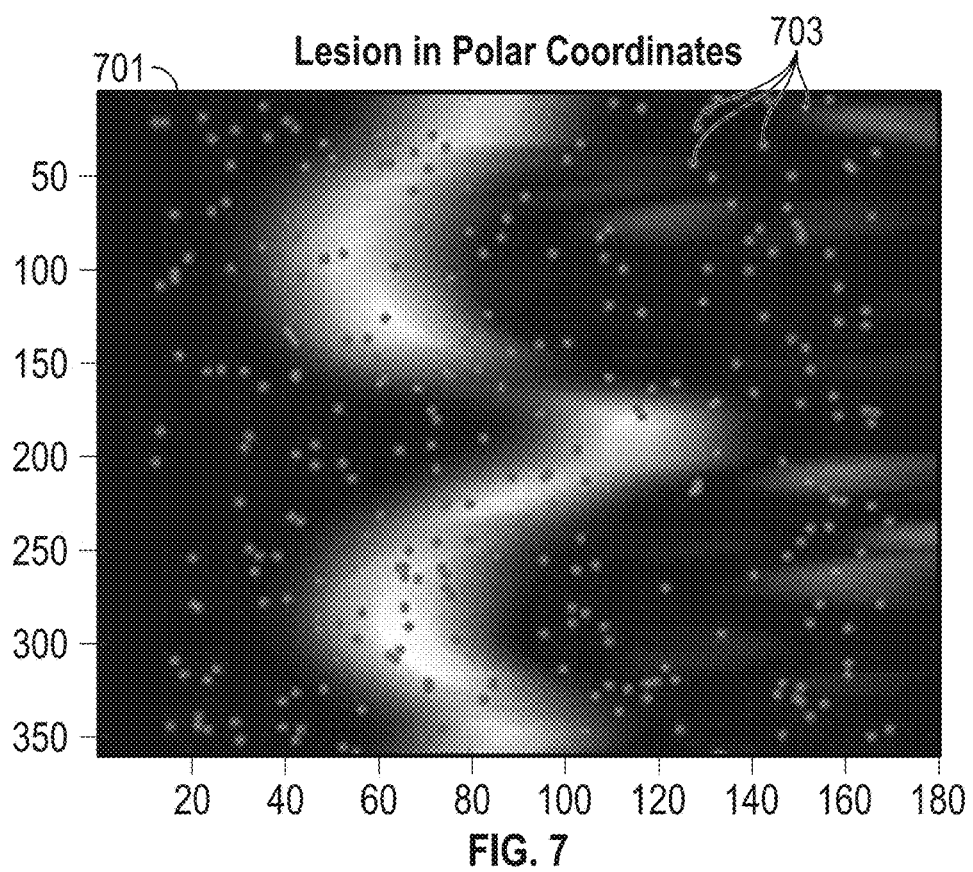
FIG. 7 is an illustration of a polar image of the resulting reflection image of FIG. 6 in polar coordinates with random points displayed thereon.
Figure 8:
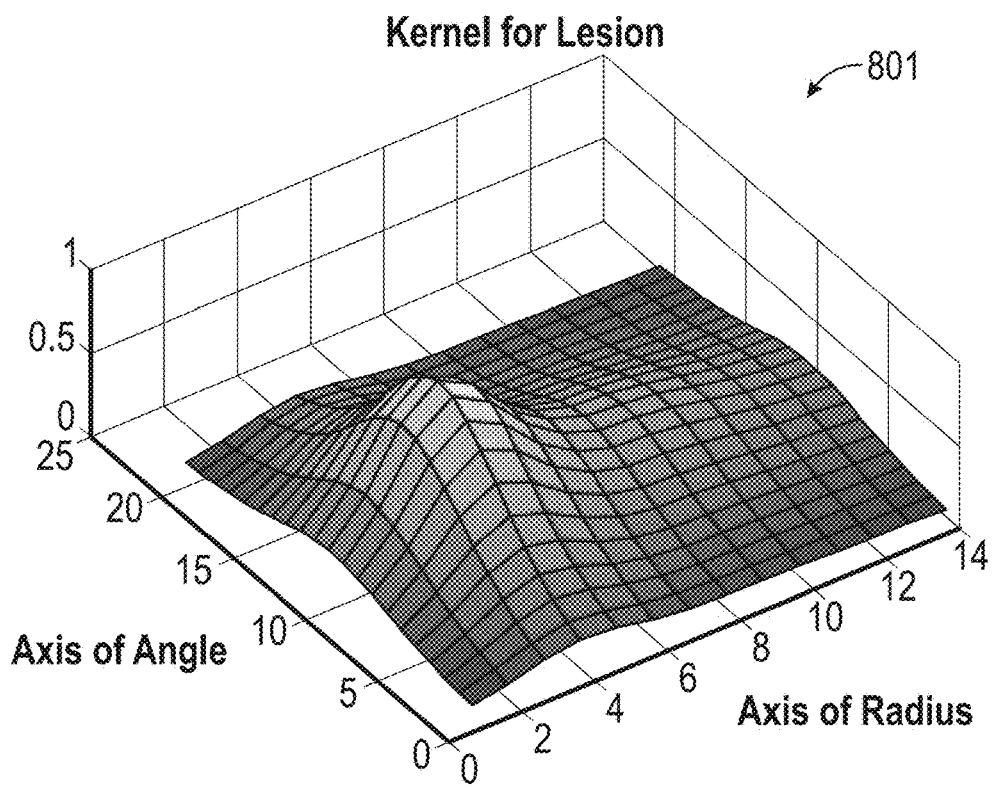
FIG. 8 is an illustration of a model kernel representing what is seen in an isolated reflection.
Figure 9:
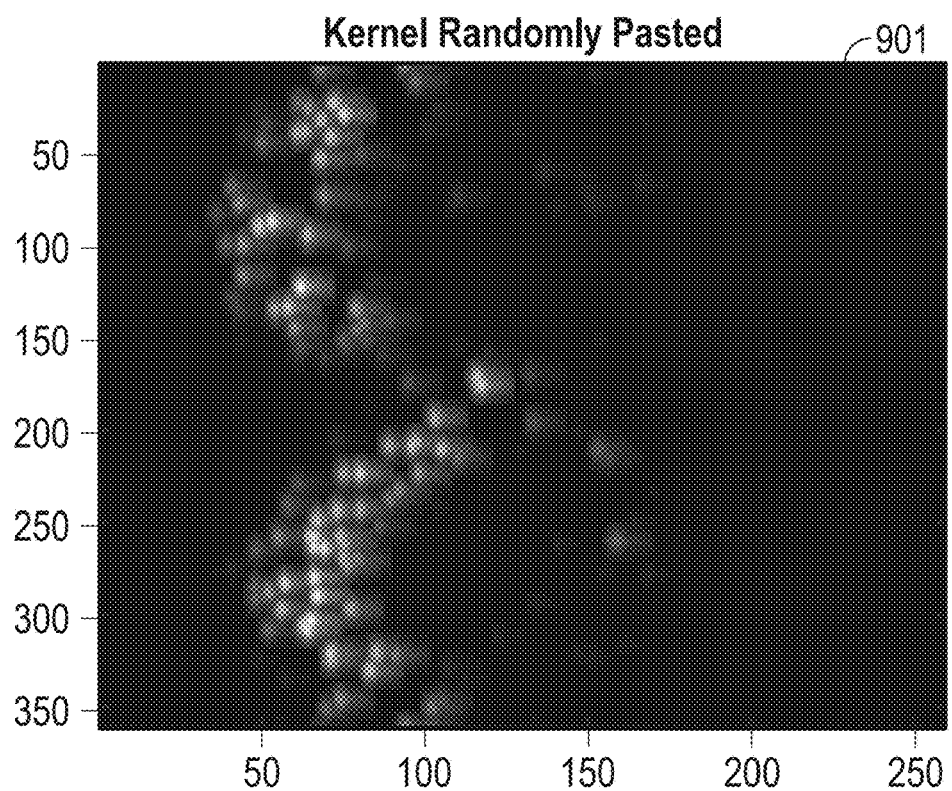
FIG. 9 is an illustration of a resulting image with the kernel randomly pasted in polar coordinates.
Figure 14:
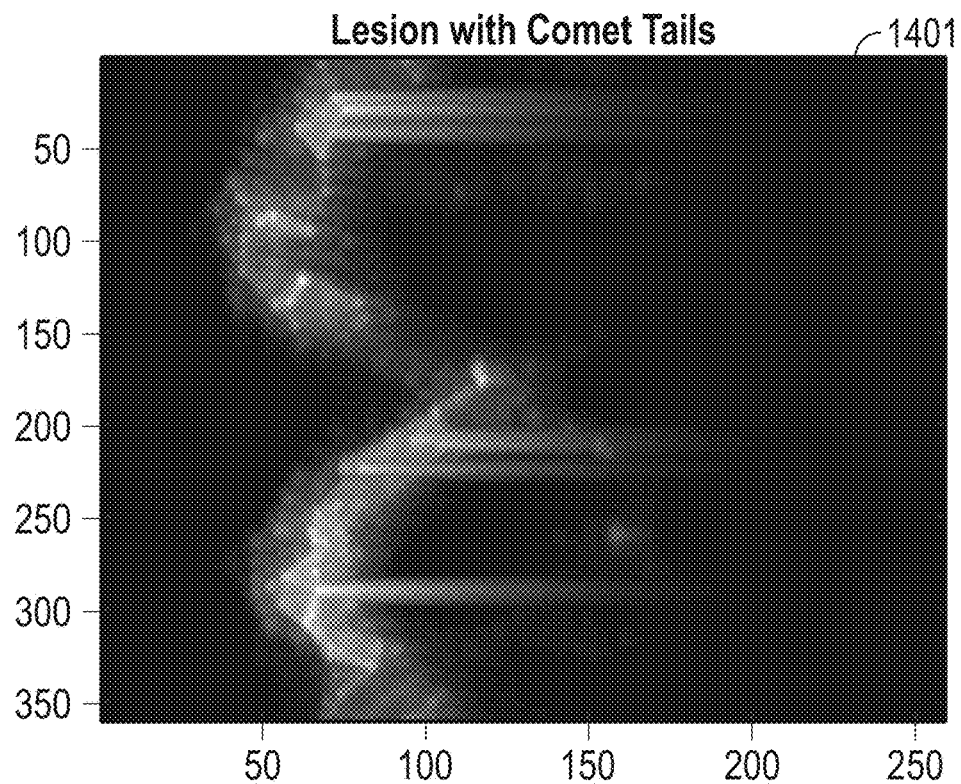
FIG. 14 is a resulting image after adding comet tails according to the difference of radius to the peak chart of FIG. 11 and the difference of angle to peak chart of FIG. 12.
Figure 15:
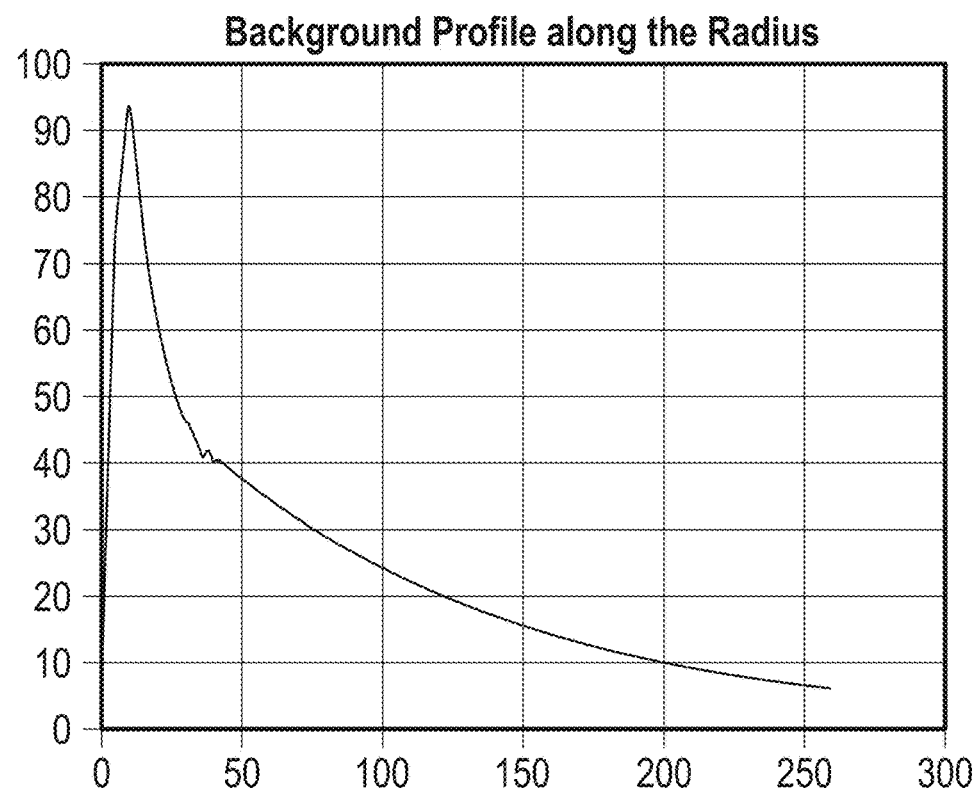
FIG. 15 is a chart showing the background profile along the radius.
Figure 16:
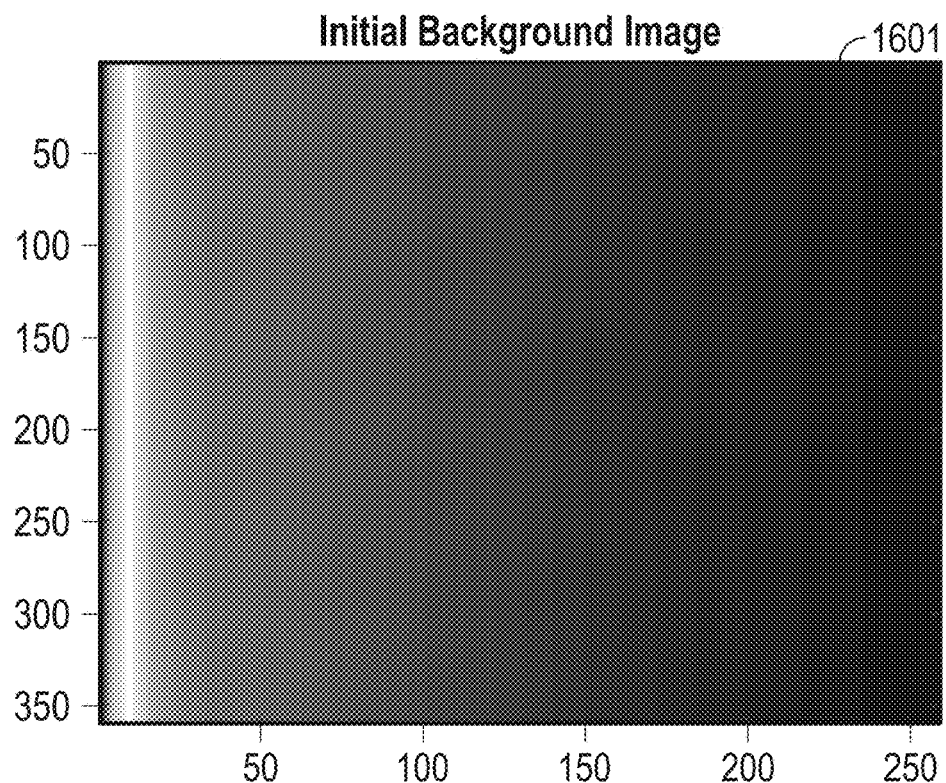
FIG. 16 is an illustration of an initial background image after the profile of FIG. 15 is copied on each row of the background image.
Figure 17:
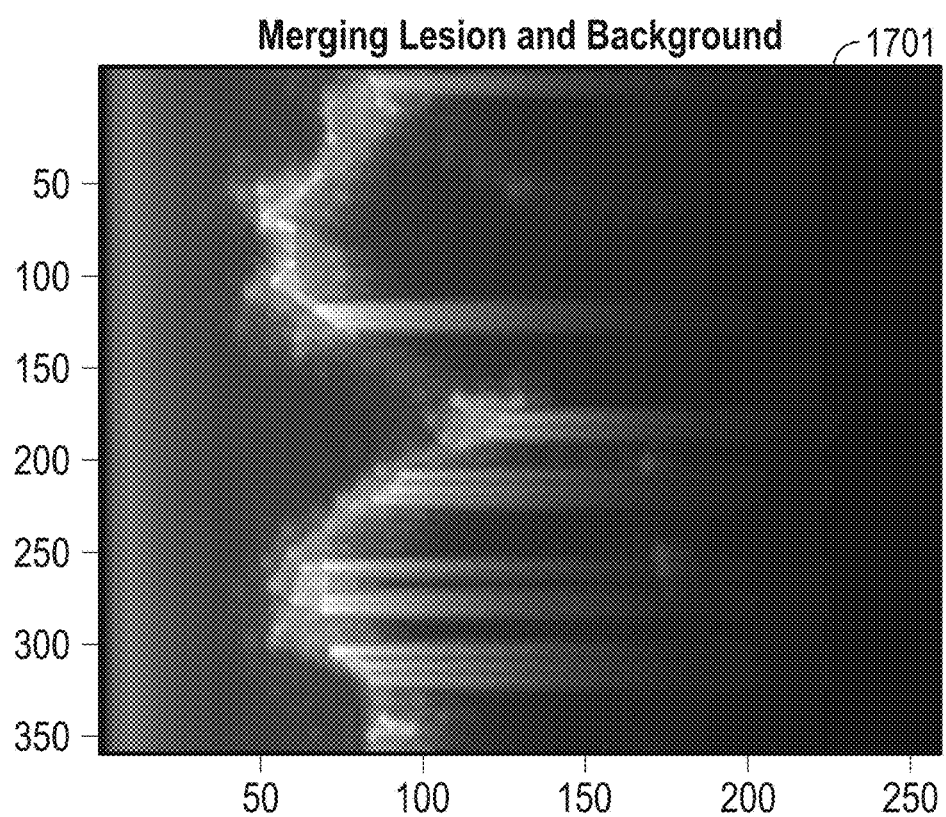
FIG. 17 is an illustration of a merged image where the initial background image of FIG. 16 is merged with the image of the lesion.
Figure 18:
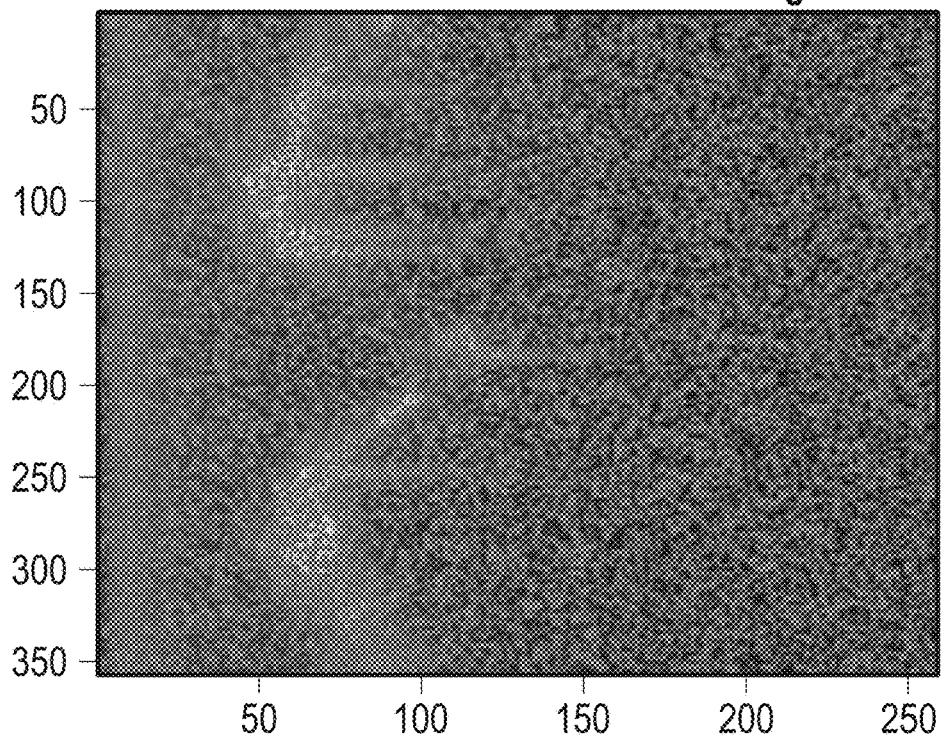
FIG. 18 is an illustration of the merged image with random locations for noise in the background simulated thereon.
Figure 19:
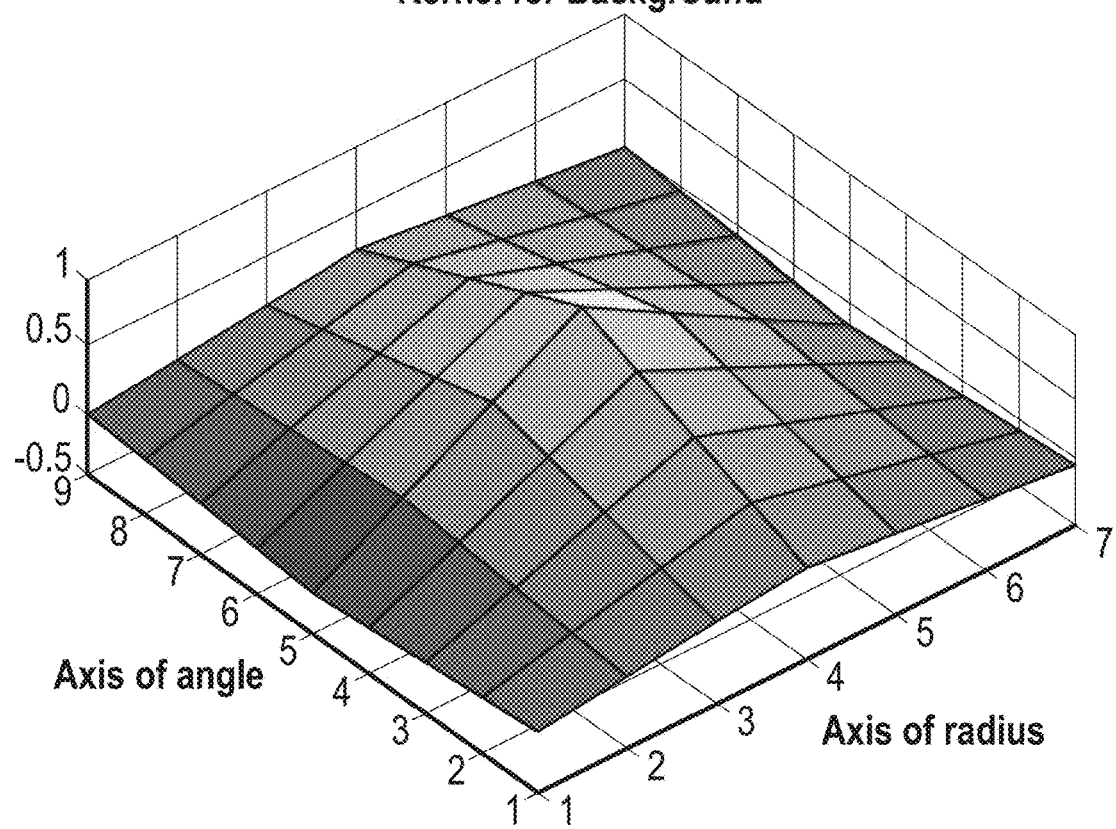
FIG. 19 is an illustration of a model kernel of a noise point.
Figure 20:
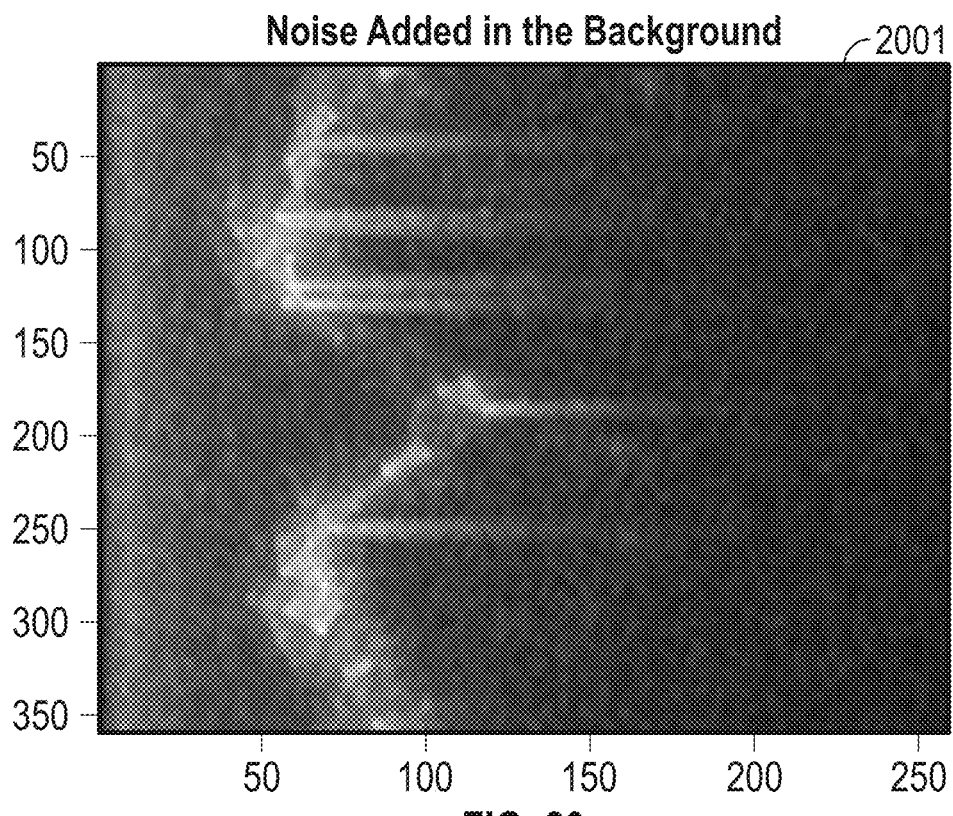
FIG. 20 is an illustration of a resulting image after noise is added in the background.
Figure 21:
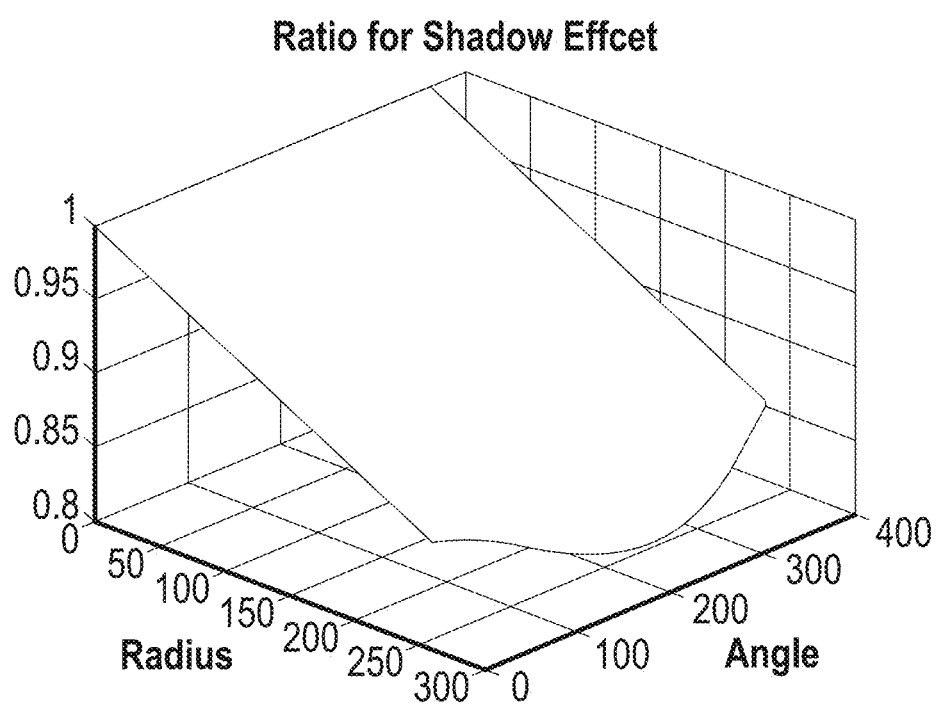
FIG. 21 is a chart for defining the ratio for applying a shadow effect.
Figure 22:
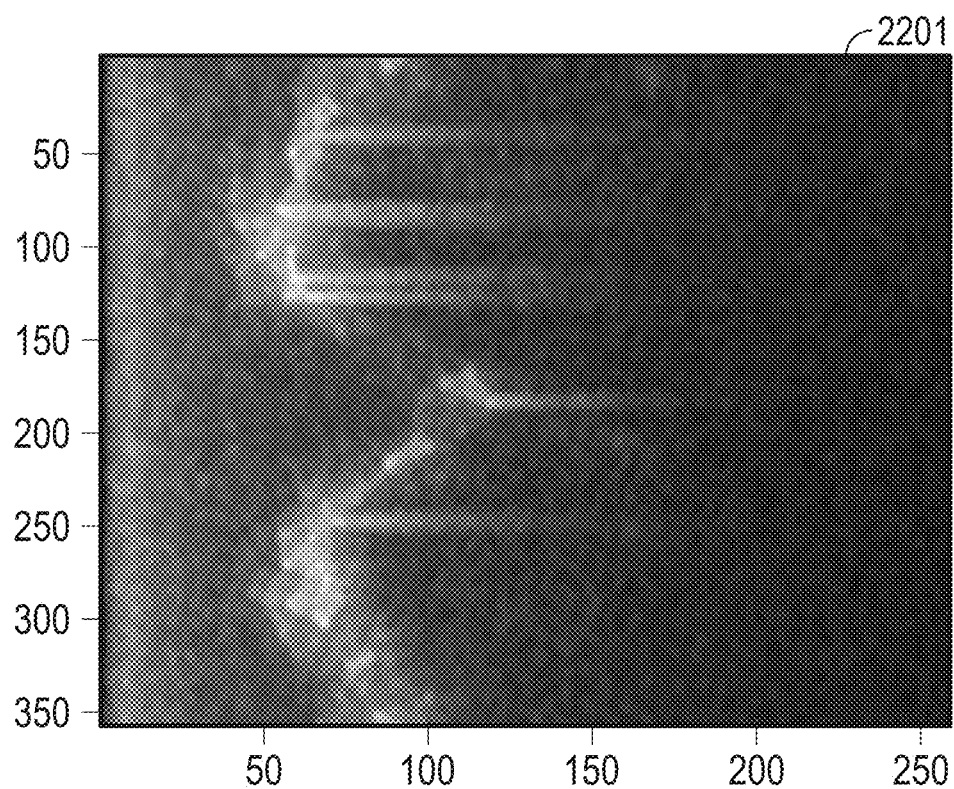
FIG. 22 is the resulting image after the shadow effect is applied.
Figure 23:
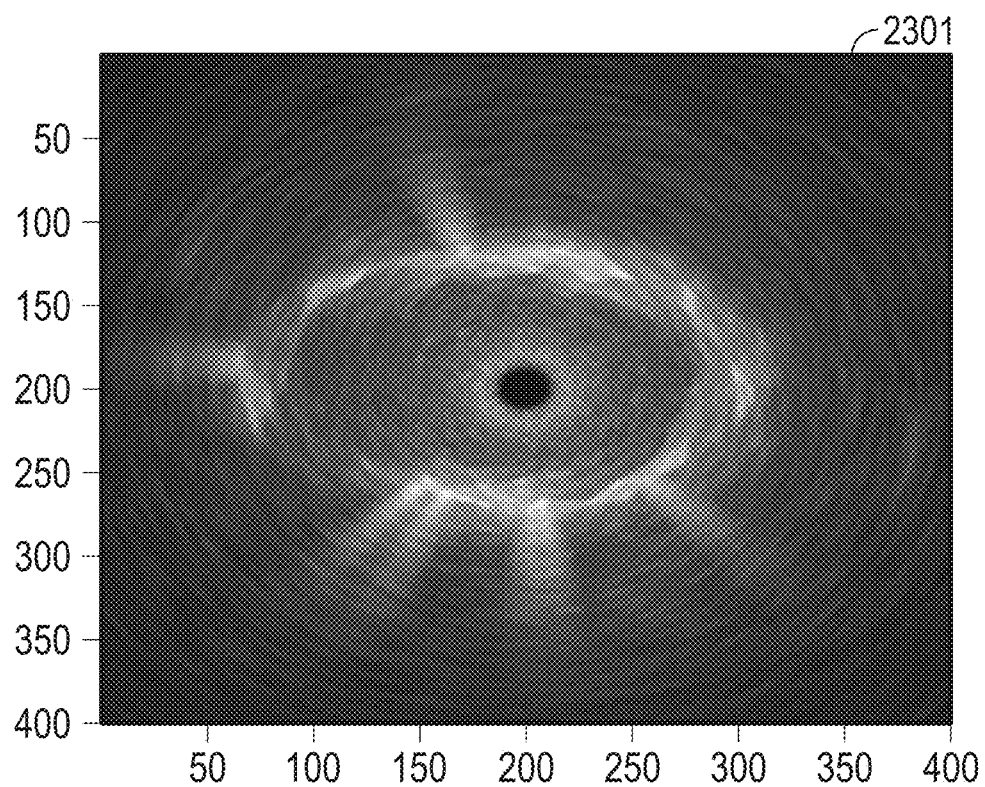
FIG. 23 is the resulting virtual radial EBUS image after transforming the coordinates to Cartesian.

Method 200 begins at step 201 where computing device 125 receives preoperative CT data of a patient's branched luminal network. In step 203, computing device 125 calculates a gradient, for example a 3D Sobel gradient, of the CT data (FIG. 3). In step 205, computing device 125 obtains 2D slices of the CT data by interpolation in 3D (FIG. 3). In step 207, computing device 125 calculates transmission and reflection values on each radial line away from a center of each 2D slice to create a lesion image (FIG. 5). In step 209, computing device 125 converts the lesion image to a polar lesion image (FIG. 7). In step 211, computing device 125 generates random noise in the polar lesion image (FIG. 9). In step 213, computing device 125 adds random comet tails to the polar lesion image based on the random noise (FIG. 14). In step 215, computing device 125 creates a background image (FIG. 16) by computing the mean profile along the radius from a series of polar lesion images. In step 217, computing device 125 merges the background image with the polar lesion image to create a merged image (FIG. 17). In step 219, computing device 125 generates random noise in the background of the merged image (FIGS. 18-20). In step 221, computing device 125 simulates density variations in the merged image (FIGS. 21-23). In step 223, computing device 125 transforms the coordinates of the merged image to Cartesian to construct a virtual radial ultrasound image (FIG. 23).

With respect to FIG. 3 and steps 203 and 205 of method 200, for the physical model, a 3D Sobel gradient with 2 pixels of step is used, however, it is understood that any gradient operator may be used. (ux1,uy1,uz1) is the 3D referential of the 3D volume considered (CT or gradient 300). (ux2,uy2,uz2) is the 3D referential of the ultrasound image, where uz2 is the direction of the probe. For each ultrasound image 301, uz2 is computed from the trajectory 303. ux2 is computed using the following formula:

$$ux2 = uy1 * uz2.$$

It is assumed that the y axis of the ultrasound is vertical (constant roll), which is not true and will be addressed in a later step. uy2 is computed using the following formula:

$$uy2 = uz2 * ux2.$$

Each point in the 2D cutting slice is defined relatively, to ux2 and uy2, so non-integer values are obtained in the 3D referential (ux2,uy2,uz2) and the 3D coordinates are derived in (ux1,uy1,uz1). Trilinear interpolation is performed between the eight neighbors (with integer coordinates).

Figure 4A:
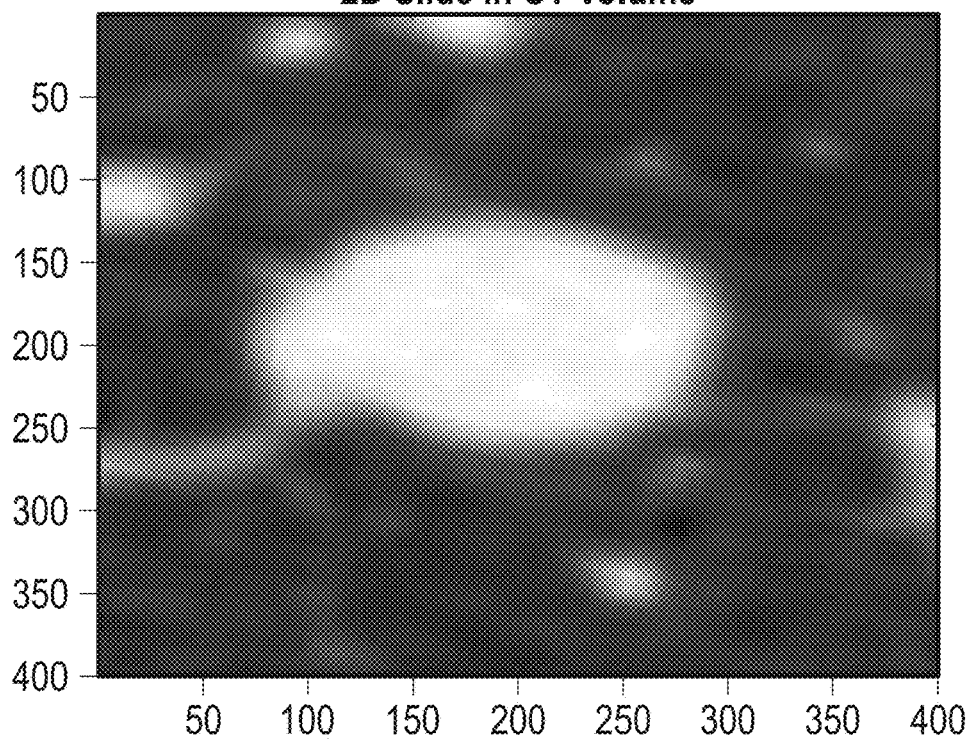
FIG. 4A is an illustration of an example of a 2D slice obtained from a CT volume.
Figure 4B:
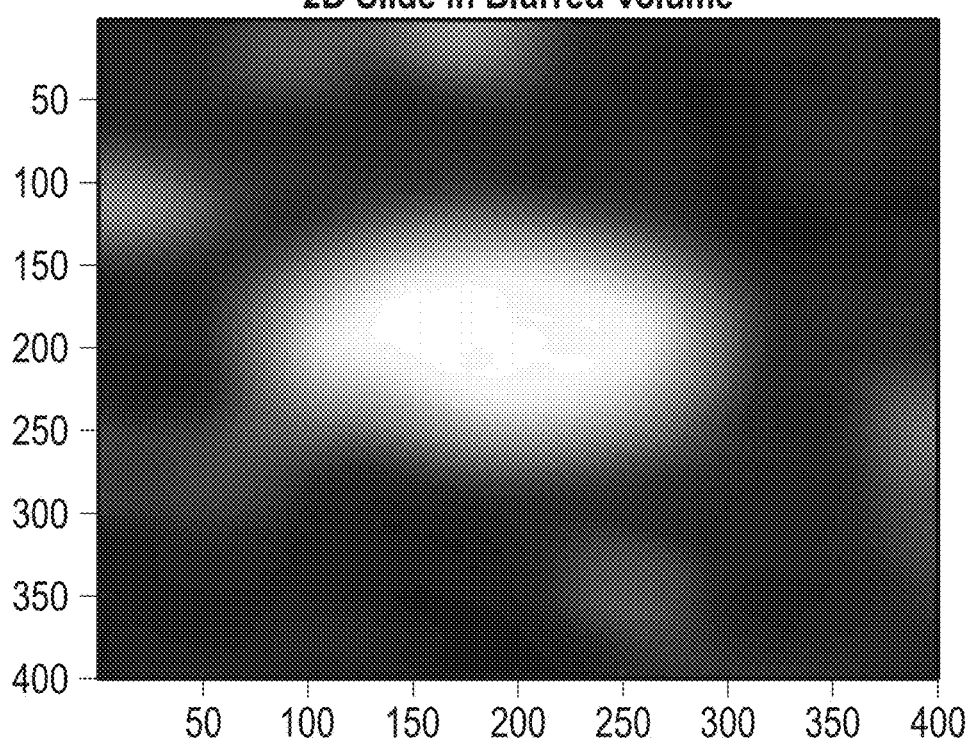
FIG. 4B is an illustration of an example of a 2D slice obtained from a blurred volume.
Figure 4C:
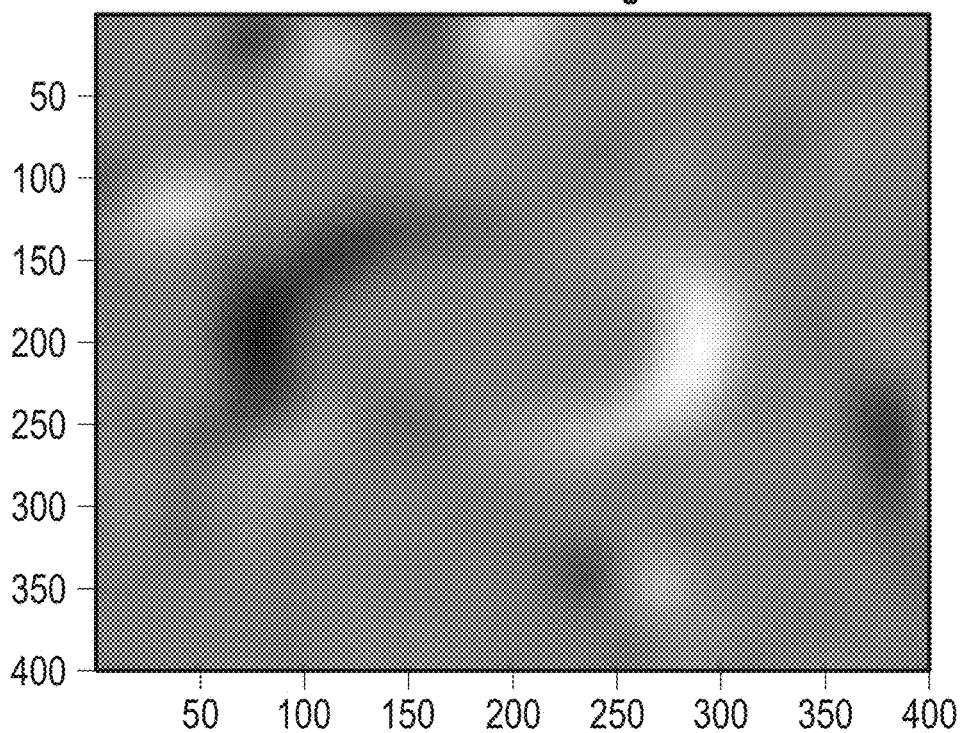
FIG. 4C is an illustration of an example of a slice (x, y) of the x-coordinate of a 3D gradient along an X axis of a CT volume.
Figure 4D:
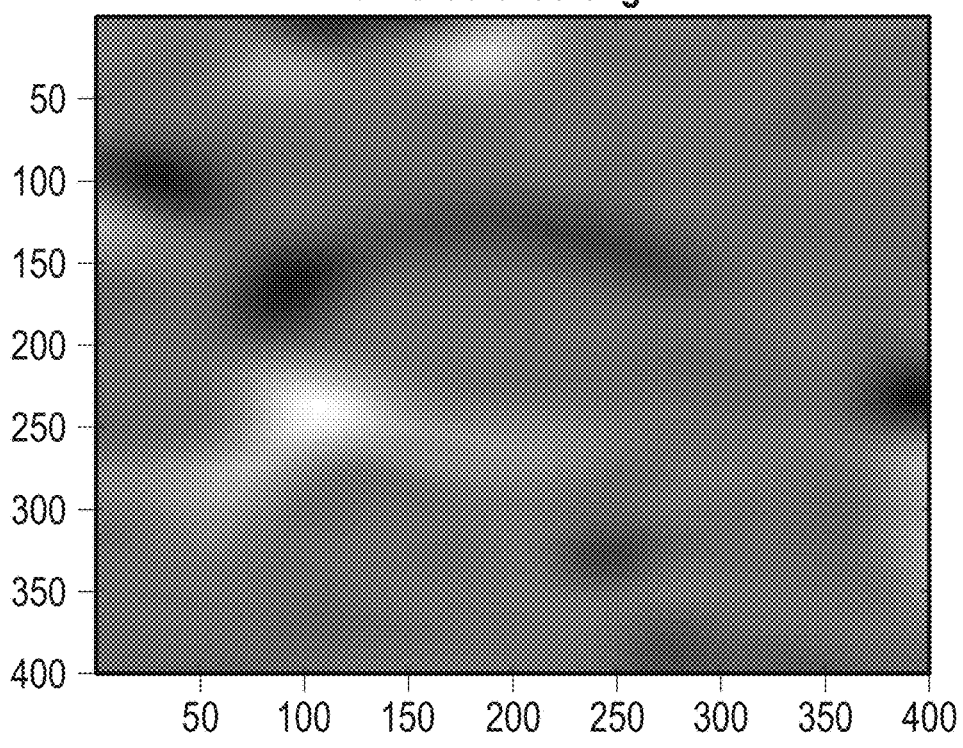
FIG. 4D is an illustration of an example of a slice (x, y) of the y-coordinate of a 3D gradient along a Y axis of a CT volume.

A blurred volume is used instead of the CT volume to avoid singularities in the steps that follow when dividing the gradient by zero values. The data is blurred with a mask, for example a Sobel mask. In particular, FIG. 4A illustrates a 2D slice obtained from the CT volume before blurring and FIG. 4B illustrates a 2D slice of the blurred volume. FIGS. 4A and 4C illustrates the 3D gradient along the X axis and the Y axis, respectively.

Figure 6:
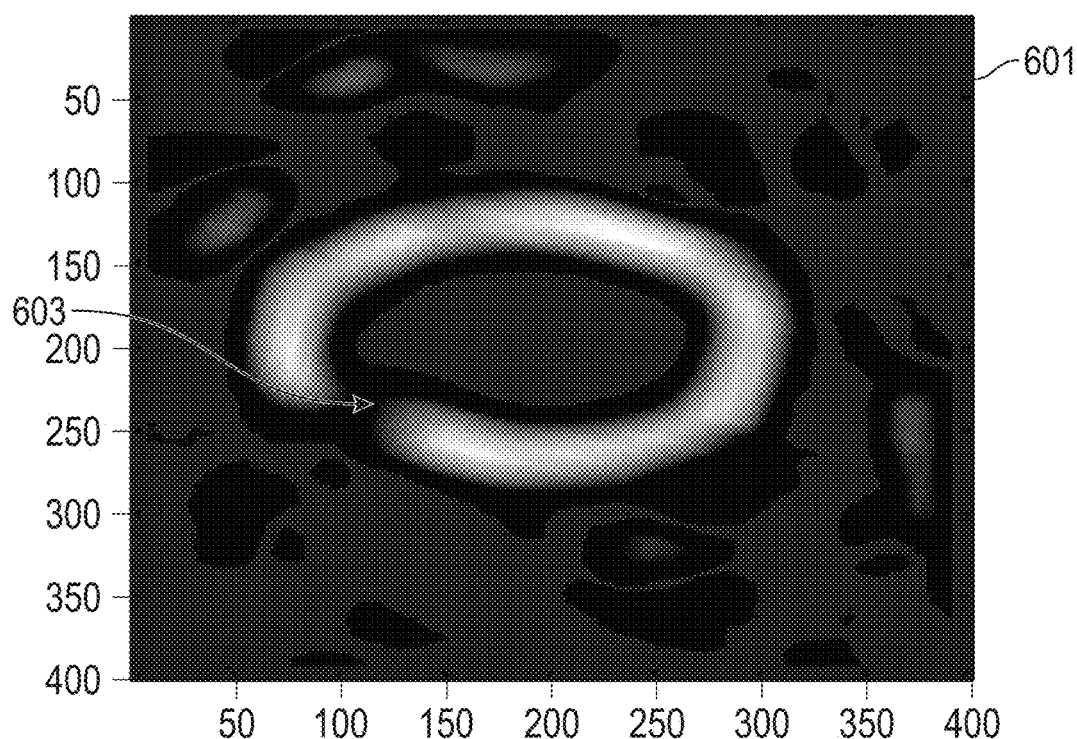
FIG. 6 is an illustration of a resulting reflection image, without noise, of a lesion.

With respect to step 207 of method 200, the transmission and reflection for creating the virtual radial EBUS image will now be described with reference to FIG. 5. Two 2D images are defined, imVirt and imTransmit. imVirt is the result image which contains the reflected signal. imTransmit contains the transmitted data and is a temporary image. Two loops are performed, an external loop and an internal loop. The external loop is performed along an angle, scanning the border points of the image ptBor. The internal loop is performed by scanning the points on the line 505 joining the central point ptCen to the border point ptBor, starting on the perimeter of the central disk 507. The unit vector Rad of line 505 is computed in 3D. The current point ptCur and the previous point ptPrev on line 505 are computed. valTransmit is defined as the value 1 on the perimeter of central disk 507. The following formulas for reflection and transmission at ptCur are applied (see FIG. 5):

$$imVirt(ptCur) = |Rad \cdot Grad| \cdot |Grad|/(2 \cdot Vol)^2 \cdot valTransmit,$$

which is the product of: the cosines of the incident angle, with the squared relative density attenuation, and with the incoming signal; and $$imTransmit(ptCur) = (1 - (|Grad|/(2 \cdot Vol))^2,$$

which is the non-reflected signal. For expediency, each value of imVirt can be computed for only a single angle. The resulting reflection image 601 is illustrated in FIG. 6, with an opening or hole 603 in the contour, representing the portion of a lesion connected to a blood vessel.

Noise on the Lesion

As described in further detail below, the disclosed methods model background noise and various types of artifacts in order to form a simulated ultrasound image that is as realistic, and as close to a real ultrasound image, as possible. The disclosed methods find an underlying probabilistic model to real ultrasound films, reverse engineering from true data. In the methods disclosed herein, as with real images, the noise gets rougher, or more exaggerated, as the distance from the center increases. In order to get a realistic simulation using this approach, most computations are performed in polar coordinates.

The reflection image 601 (FIG. 6) is shown as a polar image 701 in FIG. 7 after the lesion image is converted to a polar image in step 209 of method 200. With respect to step 211 of method 200, random points (for example, five hundred random points) are defined as represented by points 703 (e.g., 703 . . . n) in FIG. 7. A model kernel 801 (FIG. 8) is defined from several hundred sample peaks in lesions from real ultrasound images. The model kernel 801 represents what is seen in isolated reflection. For larger regions of reflection, the peaks interact. For each random peak, the kernel in the image of lesions is copied, with the amplitude defined by the gray value in the image of reflection at the location of the peak. In the formula below, neiY and neiX are lists of coordinates in the neighborhood of peakX and peakY:

imLesion(neiY,neiX)=max(imLesion(neiY,neiX), kernel*imReflection(peakY,peakX)).

The resulting image of lesions is illustrated in FIG. 9 as image 901, where relevant gray values are obtained by multiplying by 6,000. That is, the image imLesion is scaled, multiplied by 6,000, to get values of similar scope as in real ultrasound images.

Figure 10:
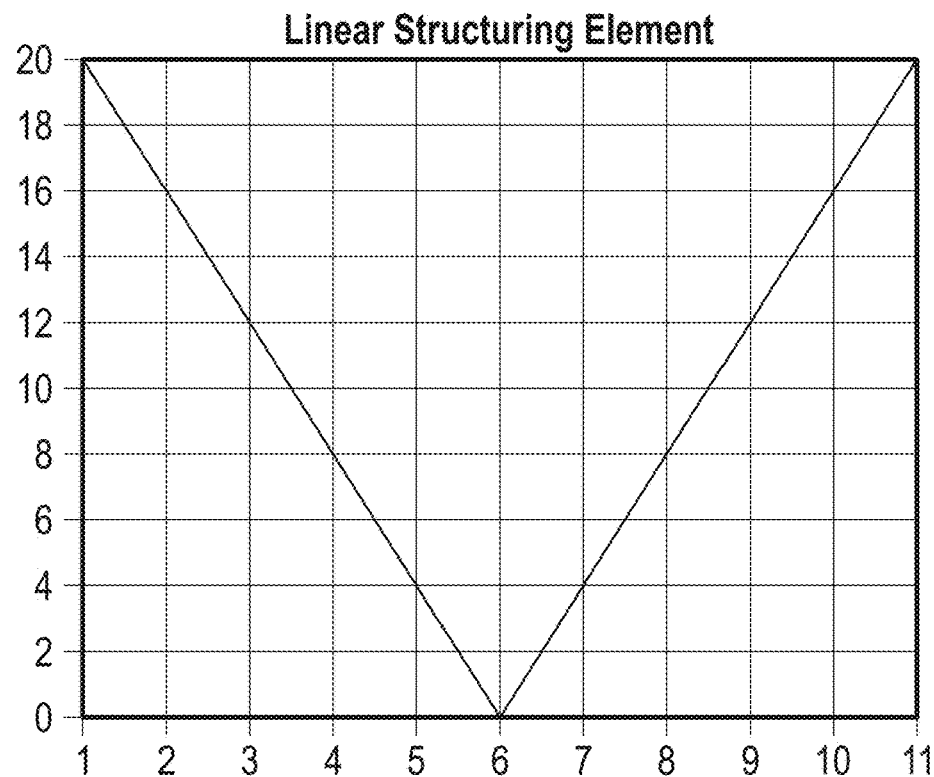
FIG. 10 is a linear structuring element chart for performing linear closings (where close peaks have been connected) for twenty different directions between 0 and 180 degrees to simulate apparent blurring in real ultrasound images around high density points.
Figure 11:
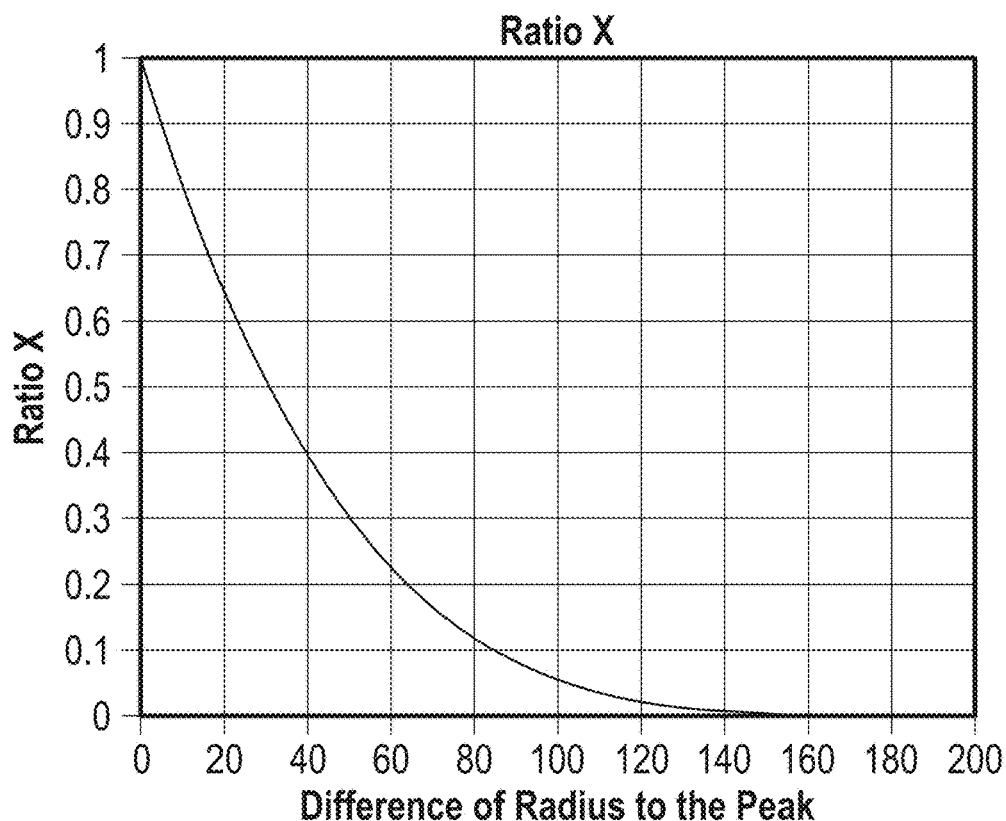
FIG. 11 is a difference of radius to the peak chart representing the radius difference to the peak ("radiusDif") for each pixel along a profile for adding comet tails, as used in the formulas described herein.
Figure 12:
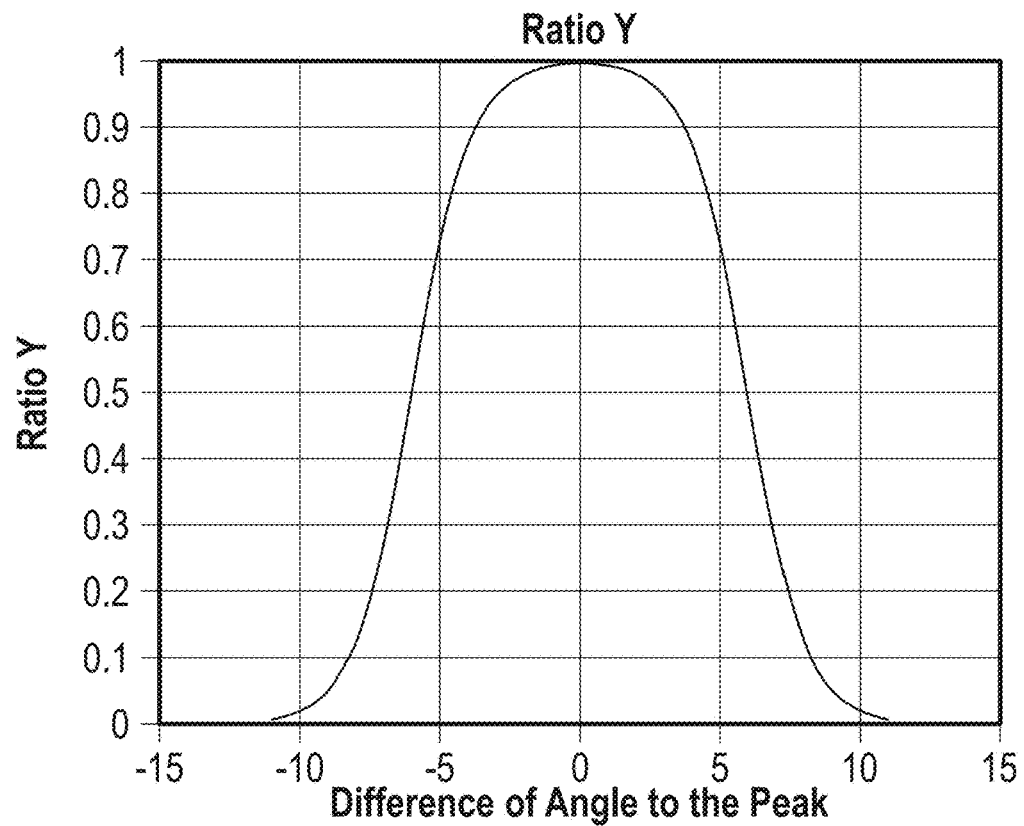
FIG. 12 is a difference of angle to the peak chart representing the angle difference to the peak ("angleDif") for each pixel along a profile for adding comet tails, as used in the formulas described herein.
Figure 13:
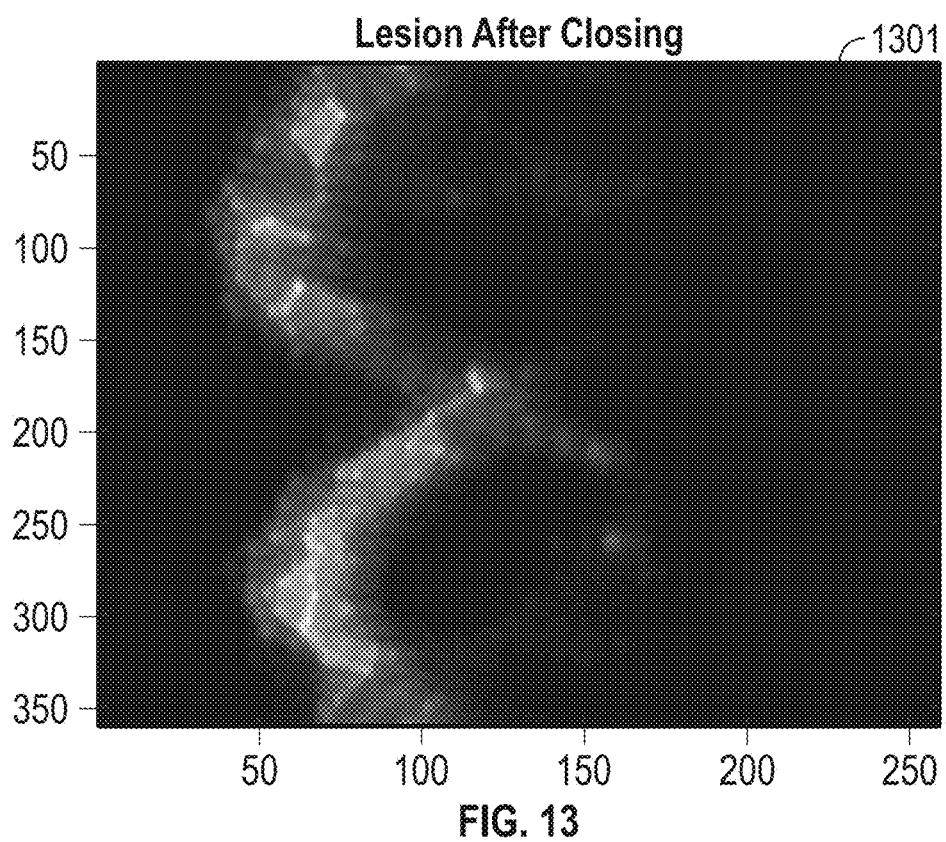
FIG. 13 is a resulting image after performing closings according to the linear structuring element chart of FIG. 10.

To simulate the apparent blurring in real ultrasound images around high density points, a plurality, for example twenty, grey linear morphological closings are performed for a plurality, for example twenty, different directions between 0 and 180 degrees (see FIG. 10, the linear structuring element used). The use of a non-flat structuring element provides a reduced grey level between two peaks to be visually joined by a segment. The resulting image is illustrated in FIG. 13 as image 1301. Additionally, the artifacts of comet tails are added to a peak if it belongs to the 10% highest peaks in the image (taking into account all peaks including those in black regions), and randomly in 10% of these cases, resulting in the image 1401 illustrated in FIG. 14 showing a lesion with comet tails. To add a comment peak, each of the peak's neighbors neiPeak, above and below, is considered inside the kernel mask. We copy to the right of the neighbor along a horizontal line a decreasing profile defined for each pixel as:

val(neiPeak)*ratioX(radiusDif)*ratioY(angleDif), where radiusDif is the radius difference to the peak and angleDif is the angle difference, for each pixel along the profile (see FIG. 11 and FIG. 12).

With respect to step 215 of method 200, the mean profile is computed along the radius from a series of images. It is composed from constant values, partly approximated as a decreasing exponential (see FIG. 15). This profile is copied on each row of the background image (see FIG. 14) and an initial background image 1601 is created (FIG. 16). With respect to step 217 of method 200, the background and lesion images are merged according to the heuristic formula:

imBackground(y,x)=imBackground(y,x)+log(imBackground(y,x))*imLesion(y,x)*K, which means that the amplitude of the lesion on the background decreases linearly with the radius (the background is a decreasing exponential). The resulting merged image 1701 is shown in FIG. 17 after step 217 of method 200 is performed by computing device 125.

With respect to step 219 of method 200, random noise is simulated in the background by: 1) generating 40,000 random points (see FIG. 18); 2) defining a kernel of "noise point" from statistics measures in a series of images (see FIG. 19); and 3) applying the following formula for each random point:

imBackground(ly,lx)=imBackground(ly,lx)+log(imBackground(ly,lx))*kernel_background, where ly and lx are the neighboring rows and columns of the random point inside the kernel. The resulting image 2001 is shown in FIG. 20 after completion of step 219 of method 200 by computing device 125. Considering the number of points, the pasted kernels interact and produce random shapes.

With respect to step 221 of method 200, to simulate the density variations of low frequency according to the angle, the following steps are taken. First, three random values V1, V2, V3 are computed in a fixed range (around 1). Second, the polynomial polShadow(angle) of degree 3 defined at the angles [0, 120, 240, 360] by the values [V1, V2, V3,V1] are computed. Third, a 2D ratio(radius,angle) (see FIG. 21) is defined where:

Ratio(minRadius,angle)=1;
Ratio(maxRadius,angle)=polShadow(angle); and
Ratio(radius, angle) is linear between minRadius and maxRadius.

Fourth, the image is multiplied by Ratio(radius,angle)^3 and the image 2201 shown in FIG. 22 is obtained. Lastly, in step 223 of method 200, the coordinates are transformed to Cartesian to obtain the virtual radial EBUS image 2301 shown in FIG. 23.

Surgical Navigation Procedure Using Virtual Radial EBUS Images

Figure 24:
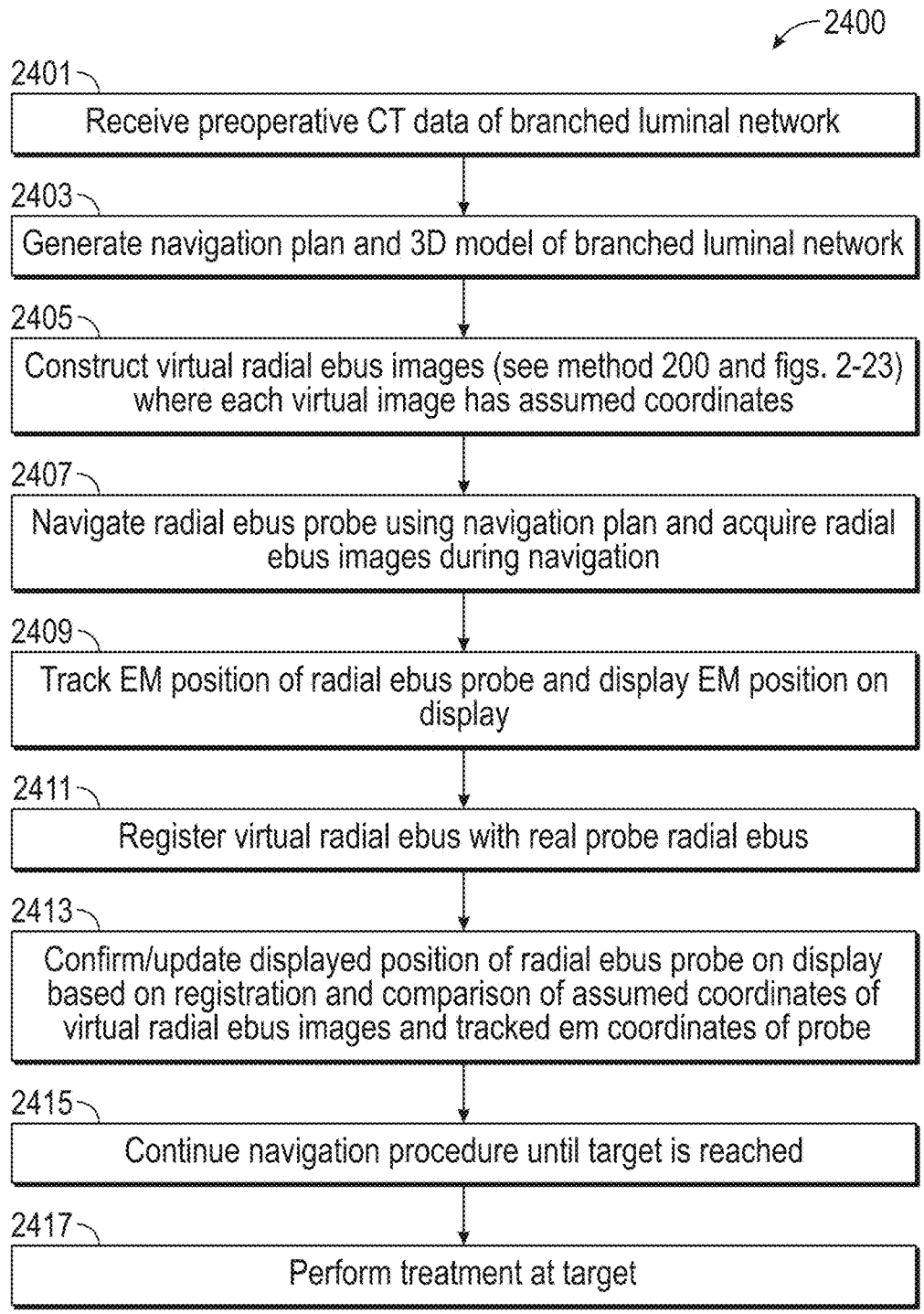
FIG. 24 is a flow chart of a method of performing a surgical navigation procedure using the system of FIG. 1.

Having described the construction of the virtual radial EBUS image above with respect to method 200 and FIGS. 2-23, a method of performing a surgical navigation procedure using system 100 will now be described as method 2400, with specific reference to FIG. 1 and FIG. 24.

As shown in FIG. 1, EWC 12 is part of a catheter guide assembly 40. In practice, the EWC 12 is inserted into bronchoscope 30 for access to a luminal network of the patient "P." Specifically, EWC 12 of catheter guide assembly 40 may be inserted into a working channel of bronchoscope 30 for navigation through a patient's luminal network. A locatable guide (LG) 32, including a sensor 44 is inserted into the EWC 12 and locked into position such that the sensor 44 extends a desired distance beyond the distal tip of the EWC 12. The position and orientation of the sensor 44 relative to the reference coordinate system, and thus the distal portion of the EWC 12, within an electromagnetic field can be derived. Catheter guide assemblies 40 are currently marketed and sold by Medtronic PLC under the brand names SUPERDIMENSION® Procedure Kits, or EDGE™ Procedure Kits, and are contemplated as useable with the present disclosure. For a more detailed description of the catheter guide assemblies 40, reference is made to commonly-owned U.S. Pat. No. 9,247,992, filed on Mar. 15, 2013, by Ladtkow et al, U.S. Pat. Nos. 7,233,820, and 9,044,254, the entire contents of each of which are hereby incorporated by reference.

An ultrasonic imaging device 45 capable of acquiring ultrasonic images or video of the patient "P" is also included in this particular aspect of system 100. The images, series of images, or video captured by the ultrasonic imaging device 45 may be stored within the ultrasonic imaging device 45 or transmitted to computing device 125 for storage, processing, registration with other data sets, and display. Additionally, the ultrasonic imaging device 45 may be a radial EBUS probe that can be inserted through a working channel of the bronchoscope 40 or more specifically, through the EWC 12 of catheter guide assembly 40 for navigation to peripheral regions of a luminal network.

With respect to the planning phase, computing device 125 utilizes previously acquired CT image data for generating and viewing a three dimensional model of the patient's "P's" airways, enables the identification of a target on the three dimensional model (automatically, semi-automatically, or manually), and allows for determining a pathway through the patient's "P's" airways to tissue located at and around the target. More specifically, CT images acquired from previous CT scans are processed and assembled into a three dimensional CT volume, which is then utilized to generate a three dimensional model of the patient's "P's" airways. The three dimensional model may be displayed on a display associated with computing device 125, or in any other suitable fashion. Using computing device 125, various views of the three dimensional model or enhanced two dimensional images generated from the three dimensional model are presented. The enhanced two dimensional images may possess some three dimensional capabilities because they are generated from three dimensional data. The three dimensional model may be manipulated to facilitate identification of target on the three dimensional model or two dimensional images, and selection of a suitable pathway through the patient's "P's" airways to access tissue located at the target can be made. Once selected, the pathway plan, three dimensional model, and images derived therefrom, can be saved and exported to a navigation system for use during the navigation phase(s). One such planning software is the ILOGIC® planning suite currently sold by Medtronic PLC.

With respect to the navigation phase, a six degrees-of-freedom electromagnetic tracking system 50, e.g., similar to those disclosed in U.S. Pat. Nos. 8,467,589, 6,188,355, and published PCT Application Nos. WO 00/10456 and WO 01/67035, the entire contents of each of which are incorporated herein by reference, or other suitable positioning measuring system, is utilized for performing registration of the images and the pathway for navigation, although other configurations are also contemplated. Tracking system 50 includes a tracking module 52, a plurality of reference sensors 54, and a transmitter mat 56. Tracking system 50 is configured for use with a locatable guide 32, particularly sensor 44, and ultrasonic imaging device 45. As described above, locatable guide 32 and sensor 44 are configured for insertion through an EWC 12 into a patient's "P's" airways (either with or without bronchoscope 30) and are selectively lockable relative to one another via a locking mechanism.

Transmitter mat 56 is positioned beneath patient "P." Transmitter mat 56 generates an electromagnetic field around at least a portion of the patient "P" within which the position of a plurality of reference sensors 54 and the sensor element 44 can be determined with use of a tracking module 52. One or more of reference sensors 54 are attached to the chest of the patient "P." The six degrees of freedom coordinates of reference sensors 54 are sent to computing device 125 (which includes the appropriate software) where they are used to calculate a patient coordinate frame of reference. Registration, as detailed below, is generally performed to coordinate locations of the three dimensional model and two dimensional images from the planning phase with the patient's "P's" airways as observed through the bronchoscope 30, and allow for the navigation phase to be undertaken with precise knowledge of the location of the sensor 44 and ultrasonic imaging device 45, even in portions of the airway where the bronchoscope 30 cannot reach. Further details of such a registration technique and their implementation in luminal navigation can be found in U.S. Patent Application Pub. No. 2011/0085720, the entire content of which is incorporated herein by reference, although other suitable techniques are also contemplated.

Registration of the patient's "P's" location on the transmitter mat 56 is performed by moving LG 32 through the airways of the patient's "P." More specifically, data pertaining to locations of sensor 44, while locatable guide 32 is moving through the airways, is recorded using transmitter mat 56, reference sensors 54, and tracking module 52. A shape resulting from this location data is compared to an interior geometry of passages of the three dimensional model generated in the planning phase, and a location correlation between the shape and the three dimensional model based on the comparison is determined, e.g., utilizing the software on computing device 125. In addition, the software identifies non-tissue space (e.g., air filled cavities) in the three dimensional model. The software aligns, or registers, an image representing a location of sensor 44 with a the three dimensional model and two dimensional images generated from the three dimension model, which are based on the recorded location data and an assumption that locatable guide 32 remains located in non-tissue space in the patient's "P's" airways. Alternatively, a manual registration technique may be employed by navigating the bronchoscope 30 with the sensor 44 to pre-specified locations in the lungs of the patient "P", and manually correlating the images from the bronchoscope to the model data of the three dimensional model.

Following registration of the patient "P" to the image data and pathway plan, a user interface is displayed in the navigation software which sets for the pathway that the clinician is to follow to reach the target. One such navigation software is the ILOGIC® navigation suite currently sold by Medtronic PLC.

Once EWC 12 has been successfully navigated proximate the target as depicted on the user interface, the locatable guide 32 may be unlocked from EWC 12 and removed, leaving EWC 12 in place as a guide channel for guiding medical instruments including without limitation, optical systems, ultrasound probes such as ultrasonic imaging device 45, marker placement tools, biopsy tools, ablation tools (i.e., microwave ablation devices), laser probes, cryogenic probes, sensor probes, and aspirating needles to the target.

Method 2400 begins at step 2401 where preoperative CT data of a patient's branched luminal network is received. In step 2403, the 3D model of the branched luminal network is generated and the navigation plan and route to one or more targets is generated. In step 2405, the virtual radial EBUS images are constructed, for example, by method 200 described above (FIGS. 2-23). In step 2405, each virtual radial EBUS image has assumed position coordinates, which may be extracted from the CT data. In step 2407, a radial EBUS probe is navigated using the navigation plan generated in step 2403. During navigation of the radial EBUS probe in step 2407, the radial EBUS probe is acquiring radial EBUS images of the patient's branched luminal network. In step 2409, the electromagnetic (EM) position of the radial EBUS probe is tracked and the position of the radial EBUS probe is displayed on a display.

In step 2411, the virtual radial EBUS images (constructed in step 2405) are registered to the real radial EBUS images (acquired by radial EBUS probe in step 2407). This registration in step 2411 may be accomplished, for example, by image-based analysis. Alternatively, or in addition, the registration in step 2411 may be accomplished by location-based analysis, where the assumed coordinates of the virtual radial EBUS images are compared to the actual coordinates of the real radial EBUS images. In one aspect, step 2411 includes utilizing registration techniques including both image-based and location-based analysis.

In step 2413, the displayed position of the radial EBUS probe is confirmed or updated on the display, based on the registration in step 2411 and a comparison of the assumed coordinates of the virtual radial EBUS images and the tracked EM position data of the radial EBUS probe. In step 2415, the navigation procedure is continued until the target is reached and in step 2417, a treatment (e.g., biopsy) is performed at the target. In order to better visualize the branched luminal network and the target, portions of the CT data may be extracted and overlaid onto the virtual radial EBUS images.

From the foregoing and with reference to the various figure drawings, those skilled in the art will appreciate that certain modifications can also be made to the present disclosure without departing from the scope of the same. For example, although the systems and methods are described as usable with an EMN system for navigation through a luminal network such as the lungs, the systems and methods described herein may be utilized with systems that utilize other navigation and treatment devices such as percutaneous devices. Additionally, although the above-described system and method is described as used within a patient's luminal network, it is appreciated that the above-described systems and methods may be utilized in other target regions such as the liver. Further, the above-described systems and methods are also usable for transthoracic needle aspiration procedures.

Detailed embodiments of the present disclosure are disclosed herein. However, the disclosed embodiments are merely examples of the disclosure, which may be embodied in various forms and aspects. Therefore, specific structural and functional details disclosed herein are not to be interpreted as limiting, but merely as a basis for the claims and as a representative basis for teaching one skilled in the art to variously employ the present disclosure in virtually any appropriately detailed structure.

As can be appreciated a medical instrument such as a biopsy tool or an energy device, such as a microwave ablation catheter, that is positionable through one or more branched luminal networks of a patient to treat tissue may prove useful in the surgical arena and the present disclosure is directed to systems and methods that are usable with such instruments and tools. Access to luminal networks may be percutaneous or through natural orifice using navigation techniques. Additionally, navigation through a luminal network may be accomplished using image-guidance. These image-guidance systems may be separate or integrated with the energy device or a separate access tool and may include MRI, CT, fluoroscopy, ultrasound, electrical impedance tomography, optical, and/or device tracking systems. Methodologies for locating the access tool include EM, IR, echolocation, optical, and others. Tracking systems may be integrated to an imaging device, where tracking is done in virtual space or fused with preoperative or live images. In some cases the treatment target may be directly accessed from within the lumen, such as for the treatment of the endobronchial wall for COPD, Asthma, lung cancer, etc. In other cases, the energy device and/or an additional access tool may be required to pierce the lumen and extend into other tissues to reach the target, such as for the treatment of disease within the parenchyma. Final localization and confirmation of energy device or tool placement may be performed with imaging and/or navigational guidance using a standard fluoroscopic imaging device incorporated with methods and systems described above.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method for constructing virtual radial ultrasonic images from CT data, the method comprising:
   receiving preoperative CT data of a branched luminal network;
   calculating a gradient of the CT data;
   obtaining 2D slices of the CT data by interpolation in 3D;
   calculating transmission and reflection values on radial lines away from a center of each 2D slice to create a lesion image;
   converting the lesion image to a polar lesion image;
   generating random noise in the polar lesion image;
   adding random comet tails to the polar lesion image based on the random noise;
   creating a background image by computing a mean profile along a radius from a series of polar lesion images;
   merging the background image with the polar lesion image to create a merged image;
   generating random noise in a background of the merged image;
   simulating density variations in the merged image; and
   transforming coordinates of the merged image to Cartesian to construct a virtual radial ultrasound image.

2. The method according to claim 1, wherein calculating transmission and reflection values on each radial line away from a center of each 2D slice to create a lesion image includes applying the formulas:

$$\text{imVirt(ptCur)}=|\text{Rad}\cdot\text{Grad}|\cdot|\text{Grad}|/(2\cdot\text{Vol})$$
$$\char`\^2\cdot\text{valTransmit; and}$$

$$\text{imTransmit(ptCur)}=(1-(|\text{Grad}|/(2\cdot\text{Vol})))\char`\^2.$$

3. The method according to claim 1, further comprising copying a kernel in the polar lesion image using a model kernel representing what is seen in an isolated reflection.

4. The method according to claim 3, wherein copying a kernel in the polar lesion image using a model kernel representing what is seen in an isolated reflection includes applying the formula:

$$\text{imLesion(neiY,neiX)=max(imLesion(neiY,neiX),}$$
$$\text{kernel}*\text{imReflection(peakY,peakX))}$$

where neiY and neiX are lists of coordinates in a neighborhood of peakY and peakX.

5. The method according to claim 1, further comprising simulating blurring of real ultrasound images around high density points in the polar lesion image.

6. The method according to claim 1, wherein simulating blurring of real ultrasound images around high density points in the polar lesion image includes performing a plurality of grey linear closings for a plurality of directions between 0 and 180 degrees.

7. The method according to claim 1, wherein adding random comet tails to the polar lesion image based on the random noise includes adding a comet to a peak by considering each neighbor of the peak (neiPeak), above and below, in a kernel mask.

8. The method according to claim 7, further comprising copying to the right of each neighbor of the peak along a horizontal line a decreasing profile defined for each pixel as:

$$\text{val(neiPeak)}*\text{ratioX(radiusDif)}*\text{ratioY(angleDif)},$$

where radiusDif is a radius difference to the peak and angleDif is an angle difference to the peak for each pixel along a profile.

9. The method according to claim 1, wherein merging the background image with the polar lesion image to create a merged image includes applying a heuristic formula.

10. The method according to claim 9, wherein the heuristic formula is:

$$imBackground(y,x)=imBackground(y,x)+\log(imBackground(y,x))*imLesion(y,x)*K.$$

11. A system for constructing virtual radial ultrasound images from CT data, comprising a computing device configured to:
receive preoperative CT data of a branched luminal network;
calculate a gradient of the CT data;
obtain 2D slices of the CT data by interpolation in 3D;
calculate transmission and reflection values on radial lines away from a center of each 2D slice to create a lesion image;
convert the lesion image to a polar lesion image;
generate random noise in the polar lesion image;
add random comet tails to the polar lesion image based on the random noise;
create a background image by computing a mean profile along a radius from a series of polar lesion images;
merge the background image with the polar lesion image to create a merged image;
generate random noise in a background of the merged image;
simulate density variations in the merged image; and
transform coordinates of the merged image to Cartesian to construct a virtual radial ultrasound image.

12. The system according to claim 11, wherein the computing device is configured to calculate transmission and reflection values on each radial line away from a center of each 2D slice to create a lesion image by applying the formulas:

$$imVirt(ptCur)=|Rad \cdot Grad|\cdot|Grad|/(2 \cdot Vol)^2 \cdot valTransmit; \text{ and}$$

$$imTransmit(ptCur)=(1-(|Grad|/(2 \cdot Vol))^2.$$

13. The system according to claim 11, wherein the computing device is further configured to copy a kernel in the polar lesion image using a model kernel representing what is seen in an isolated reflection.

14. The system according to claim 13, wherein the computing device is configured to copy a kernel in the polar lesion image using a model kernel representing what is seen in an isolated reflection by applying the formula:

$$imLesion(neiY,neiX)=\max(imLesion(neiY,neiX), kernel*imReflection(peakY,peakX))$$

where neiY and neiX are lists of coordinates in a neighborhood of peakY and peakX.

15. The system according to claim 11, wherein the computing device is further configured to simulate blurring of real ultrasound images around high density points in the polar lesion image.

16. The system according to claim 11, wherein the computing device is configured to simulate blurring of real ultrasound images around high density points in the polar lesion image by performing a plurality of grey linear closings for a plurality of directions between 0 and 180 degrees.

17. The system according to claim 11, wherein the computing device is configured to add random comet tails to the polar lesion image based on the random noise by adding a comet to a peak by considering each neighbor of the peak (neiPeak), above and below, in a kernel mask.

18. The system according to claim 17, wherein the computing device is further configured to copy to the right of each neighbor of the peak along a horizontal line a decreasing profile defined for each pixel as:

$$val(neiPeak)*ratioX(radiusDif)*ratioY(angleDif),$$

where radiusDif is a radius difference to the peak and angleDif is an angle difference to the peak for each pixel along a profile.

19. The system according to claim 11, wherein the computing device is configured to merge the background image with the polar lesion image to create a merged image by applying a heuristic formula.

20. The system according to claim 19, wherein the heuristic formula is:

$$imBackground(y,x)=imBackground(y,x)+\log(imBackground(y,x))*imLesion(y,x)*K.$$

* * * * *